US012751764B2

(12) United States Patent
Liu

(10) Patent No.: US 12,751,764 B2
(45) Date of Patent: Oct. 6, 2026

(54) ABLATION DEVICE AND ABLATION SYSTEM

(71) Applicant: HANGZHOU DINOVA EP TECHNOLOGY CO., LTD, Hangzhou (CN)

(72) Inventor: Cheng Liu, Hangzhou (CN)

(73) Assignee: Hangzhou Dinova EP Technology Co., Ltd., Hangzhou (CN)

( * ) Notice: Subject to any disclaimer, the term of this patent is extended or adjusted under 35 U.S.C. 154(b) by 649 days.

(21) Appl. No.: 18/211,489

(22) Filed: Jun. 19, 2023

(65) Prior Publication Data

US 2023/0329780 A1 Oct. 19, 2023

Related U.S. Application Data

(63) Continuation of application No. PCT/CN2021/143718, filed on Dec. 31, 2021.

(30) Foreign Application Priority Data

Dec. 31, 2020 (CN) ......................... 202011644953.3

(51) Int. Cl.
*A61B 18/14* (2006.01)
*A61B 18/00* (2006.01)

(52) U.S. Cl.
CPC *A61B 18/1492* (2013.01); *A61B 2018/00577* (2013.01); *A61B 2018/00839* (2013.01)

(58) Field of Classification Search
CPC ...... A61B 18/1492; A61B 2018/00577; A61B 2018/00839; A61B 2018/00267
See application file for complete search history.

(56) References Cited

U.S. PATENT DOCUMENTS 5,681,280 A 10/1997 Rusk et al.
2002/0111618 A1 8/2002 Stewart
(Continued)

FOREIGN PATENT DOCUMENTS

CN 101797181 A 8/2010
CN 103519882 A 1/2014
(Continued)

OTHER PUBLICATIONS

PCT Search Report dated Apr. 1, 2022 for PCT/CN2021/143718.
Extended European Search Report Dated Jun. 10, 2024 for Corresponding European Application No. 21914717.0.

*Primary Examiner* — Adam Z Minchella

(57) ABSTRACT

An ablation device includes an ablation assembly and an adjustment assembly provided at the proximal end of the ablation assembly. The ablation assembly includes a support skeleton and an ablation member provided on the support skeleton. The adjustment assembly includes an inner sheath catheter, an outer sheath catheter and a diameter adjustment module. The outer and inner sheath catheters are movably sleeved in an axial direction, the distal end of the outer sheath catheter is connected to the proximal end of the support skeleton, the distal end of the inner sheath catheter is connected to the distal end of the support skeleton, and the inner sheath catheter is connected to the diameter adjustment module. The diameter adjustment module is movable in the axial direction to drive the inner sheath catheter to move axially relative to the outer sheath catheter, so that the support skeleton deforms to change its radial size.

20 Claims, 11 Drawing Sheets

(56) References Cited

U.S. PATENT DOCUMENTS

| | | | | |
|---|---|---|---|---|
| 2002/0177765 | A1* | 11/2002 | Bowe | A61B 18/1492 600/374 |
| 2004/0097819 | A1 | 5/2004 | Duarte | |
| 2004/0193239 | A1 | 9/2004 | Falwell et al. | |
| 2010/0130807 | A1 | 5/2010 | White et al. | |
| 2010/0168737 | A1 | 7/2010 | Grunewald | |
| 2010/0256627 | A1 | 10/2010 | Ma et al. | |
| 2013/0116688 | A1 | 5/2013 | Kunis et al. | |
| 2014/0257069 | A1* | 9/2014 | Eliason | A61B 5/6858 600/373 |
| 2015/0342675 | A1 | 12/2015 | Highsmith | |
| 2017/0189106 | A1* | 7/2017 | Schuler | A61B 18/02 |
| 2018/0271594 | A1* | 9/2018 | Tyson | A61B 18/1206 |
| 2021/0161582 | A1* | 6/2021 | Byrd | A61B 18/1206 |

FOREIGN PATENT DOCUMENTS

| | | | | |
|---|---|---|---|---|
| CN | 107028651 | A | 8/2017 | |
| CN | 211934282 | U | 11/2020 | |
| CN | 212015753 | U | 11/2020 | |
| WO | WO-2021126980 | A1 * | 6/2021 | A61B 18/1492 |

* cited by examiner

ABLATION DEVICE AND ABLATION SYSTEM

The present application is a Continuation Application of PCT Application No. PCT/CN2021/143718, filed Dec. 31, 2021, which claims priority to Chinese Patent Application No. 202011644953.3, filed on Dec. 31, 2020, the entire contents of which are hereby incorporated by reference.

TECHNICAL FIELD

The present invention relates to the technical field of medical equipment, and particularly relates to an ablation device and an ablation system.

BACKGROUND

Atrial fibrillation (AF) is the most common persistent arrhythmia. As people get older, the incidence of atrial fibrillation continues to increase, which is as high as 10% in people over 75 years old. During atrial fibrillation, the frequency of atrial activation of the human body can reach 300~600 beats/min, and the frequency of the heartbeat is generally fast and disorderly. During atrial fibrillation, the atria lose effective contractile function, and sometimes the frequency of the heartbeat may reach 100~160 beats/min, which is not only much faster than that of normal people, but also absolutely irregular. Atrial fibrillation generally increases the risk of many potentially fatal complications, including but not limited to thromboembolic stroke, dilated cardiomyopathy, congestive heart failure and etc. Compared with normal people, the average incidence of people with atrial fibrillation has increased five times, and the mortality has increased two times. Further, common symptoms of atrial fibrillation, such as palpitation, chest pain, dyspnea, fatigue and dizziness may also affect the quality of life of the patients.

Nowadays, one of the most commonly used methods for treating various cardiac arrhythmias is tissue ablation. Tissue ablation generally utilizes ablation catheters to ablate tissue to treat cardiac arrhythmias, such as by means of ablating tissue to prevent abnormal electrical transmission and/or destroying abnormal electrical conduction through cardiac tissue. Currently, according to the principle of ablation, ablation treatment includes two aspects: one of which is thermal ablation, such as radio frequency ablation, laser ablation, microwave ablation, thermal material ablation and etc., and the other is pulsed ablation of tissue according to the principle of bio-electroporation.

However, many current ablation catheters do not have the function of flexibly adjusting the size of the ablation member at the distal end of the ablation catheter based on the anatomical structure of the specific ablation target tissue, which results in difficulty in approaching the target tissue area, so that multiple localization and ablation procedures are required in the target tissue area, and the surgical operation is complex and time-consuming.

SUMMARY

In order to solve the above technical problems, the present invention provides an ablation device, which includes an ablation assembly and an adjustment assembly provided at the proximal end of the ablation assembly. The ablation assembly includes a support skeleton and an ablation member provided on the support skeleton. The adjustment assembly includes an inner sheath catheter, an outer sheath catheter and a diameter adjustment module, the inner sheath catheter being movably mounted in the outer sheath catheter along an axial direction, the distal end of the outer sheath catheter being connected to the proximal end of the support skeleton, the distal end of the inner sheath catheter being connected to the distal end of the support skeleton, and the inner sheath catheter being connected to the diameter adjustment module. The diameter adjustment module is movable along the axial direction to drive the inner sheath catheter to move relative to the outer sheath catheter along the axial direction, so as to make the support skeleton deform to change a radial size thereof.

The present invention further provides an ablation system, which includes a mapping device and the above ablation device. The mapping device includes a mapping catheter and a mapping member provided at the distal end of the mapping catheter. The mapping catheter is inserted in the inner sheath catheter, and the mapping member extends out from the distal end of the inner sheath catheter to contact a tissue wall for detecting electrophysiological signals in the target tissue region.

The support skeleton of the ablation device provided by the embodiments of the present invention is easy to change its radial size under the action of the diameter adjustment module to contact the target tissue region, which is conducive to simplifying the surgical procedure and reducing the difficulty of surgery.

BRIEF DESCRIPTION OF THE DRAWINGS

In order to illustrate technical solutions of embodiments of the present invention more clearly, drawings needed to be used in the embodiments will be briefly described below. It is obvious that the drawings described below are some embodiments of the present invention, and other drawings may be obtained from these drawings without any creative work to those skilled in the art.

DESCRIPTION OF THE EMBODIMENTS

Figure 1:
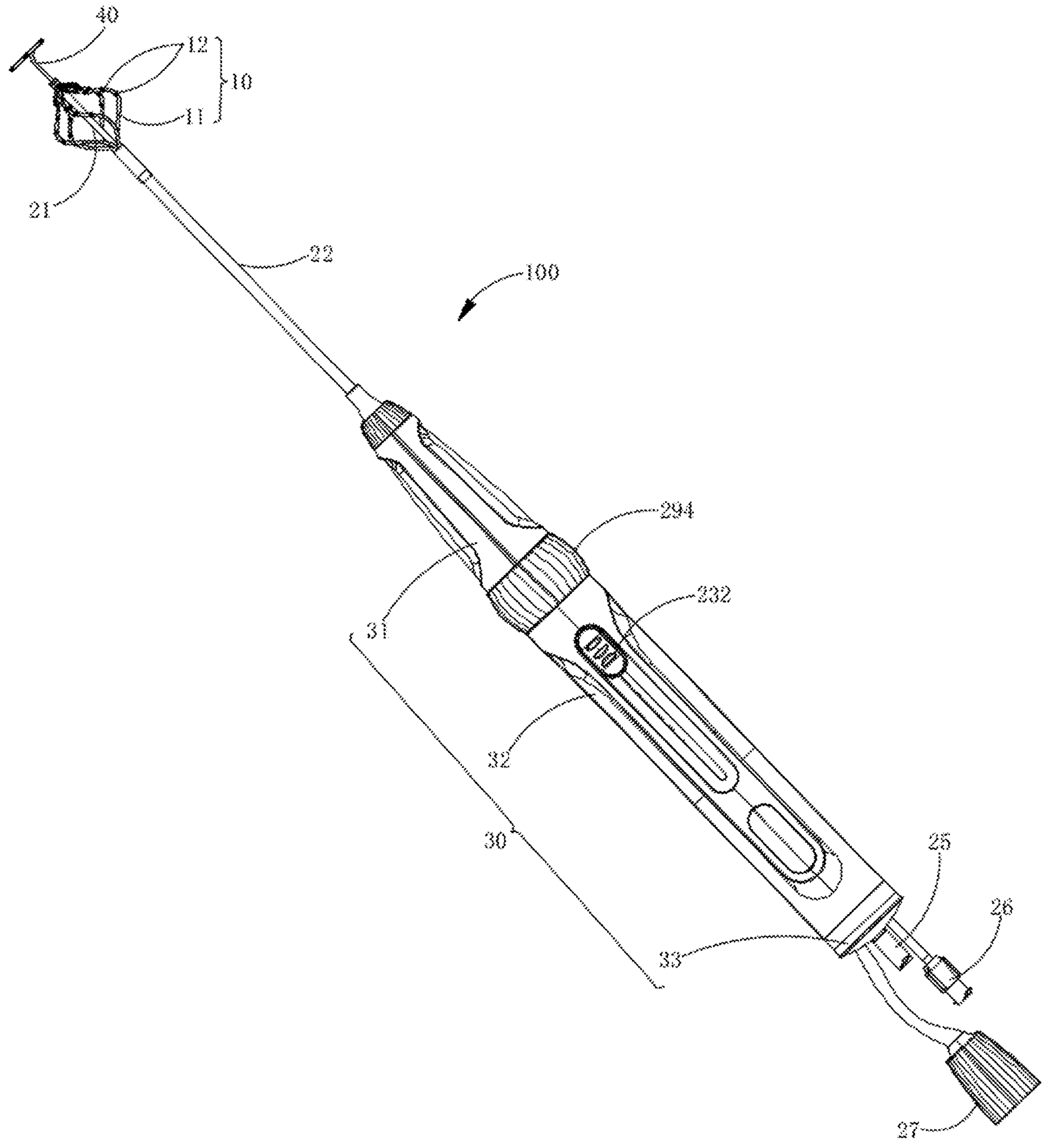
FIG. 1 is a schematic view of an ablation system provided by an embodiment of the present invention.

The technical solutions of the embodiments of the present invention will be clearly and completely described with reference to the drawings of the embodiments of the present invention. Apparently, the described embodiments are merely some embodiments, but not all of the embodiments of the present invention. All other embodiments obtained by persons of ordinary skill in the art based on the embodiments of the present invention without creative efforts shall fall within the protection scope of the present invention.

In addition, the following descriptions of the embodiments refer to appended drawings, for illustrating specific embodiments of the invention that may be implemented. The directional terms mentioned in the present invention, such as “up”, “down”, “front”, “back”, “left”, “right”, “in”, “out”, “side wall” and the like, refer only to the direction of the appended drawings. Therefore, the directional terms are used for better and clearer explanation and understanding of the present invention, rather than indicate or imply that the referred device or member must have a specific orientation, is constructed and operated in a specific orientation, and therefore cannot be understood as a limitation of the present invention.

Orientation definition: for clarity of description, “proximal end” means an end close to the operator during the surgical procedure, and “distal end” means an end remote from the operator during the surgical procedure; “axial direction” means a direction parallel to a line connecting the distal center and the proximal center of the medical equipment, and “radial direction” means a direction perpendicular to the axial direction. The above definition is only for convenience of description and is not to be considered as a limitation of the present invention. “Connection of component A and component B” means that component A is directly connected to component B or is indirectly connected to component B by other components.

Please referring to FIGS. 1-3 and FIG. 16 together, the present invention provides an ablation system, which includes an ablation device 100 and a mapping device 40. The ablation device 100 includes an ablation assembly 10, an adjustment assembly 20 and a handle 30. The handle 30 may be hollow, and the adjustment assembly 20 is provided at the proximal end of the ablation assembly 10 and partially accommodated in the handle 30. The handle 30 includes a front housing 31, a rear housing 32, and a tail housing 33 which are arranged in sequence from the distal end to the proximal end. The ablation assembly 10 includes a support skeleton 11 and an ablation member 12 provided on the support skeleton 11.

Please referring to FIG. 1 to FIG. 8 together, the adjustment assembly 20 includes an inner sheath catheter 21, an outer sheath catheter 22 and a diameter adjustment module 23. The inner sheath catheter 21 is inserted in the outer sheath catheter 22 and movable along an axial direction. The distal end of the outer sheath catheter 22 is connected to the proximal end of the support skeleton 11, the distal end of the inner sheath catheter 21 is connected to the distal end of the support skeleton 11, and the proximal end of the inner sheath catheter 21 is connected to the diameter adjustment module 23. The diameter adjustment module 23 moves along the axial direction to drive the inner sheath catheter 21 to move along the axial direction relative to the outer sheath catheter 22, making the support skeleton 11 deform to change its radial size. If the diameter adjustment module 23 moves axially towards the proximal end, it drives the inner sheath catheter 21 to move axially towards the proximal end relative to the outer sheath catheter 22, so as to enlarge the radial size of the support skeleton 11. If the diameter adjustment module 23 moves axially to the distal end, it drives the inner sheath catheter 21 to move axially to the distal end relative to the outer sheath catheter 22, so as to reduce the radial size of the support skeleton 11.

Specifically, the diameter adjustment module 23 is accommodated in the rear housing 32. The diameter adjustment module 23 includes a moving member 231 and an operating member 232 connected to the moving member 231. The inner sheath catheter 21 is fixed to the moving member 231, and movement of the operation member 232 is capable of driving the moving member 231 to move axially, thereby driving the inner sheath catheter 21 to move axially relative to the outer sheath catheter 22, making the support skeleton 11 deform to change its radial size. A specific deformation process of the support skeleton 11 will be described in detail in the description of the support skeleton 11 below.

Please referring to FIGS. 3-6, in this embodiment, the operating member 232 includes a connecting portion 2321 and a moving portion 2322 connected to the connecting portion 2321. The rear housing 32 includes a first housing 321 and a second housing 322 that are buckled to each other. The moving member 231 is accommodated between the first housing 321 and the second housing 322 in the radial direction, i.e., the moving member 231 is accommodated in an inner cavity of the rear housing 32 in the radial direction. Along the axial direction, the first housing 321 defines a travelling groove 3211 which extends through inner and outer surfaces of the first housing 321. The moving portion 2322 is movably inserted in the travelling groove 3211 and connected to the connecting portion 2321, i.e., the operating member 232 is movably inserted in the travelling groove 3211 and connected to the distal end of the moving member 231. The “first housing 321” and “second housing 322” are only for convenience of description and cannot be considered as a limitation to the present invention.

Specifically, the distal end of the moving member 231 defines a positioning slot 2311 matching with the connecting portion 2321, and the connecting portion 2321 is at least partially accommodated in the positioning slot 2311. Preferably, the moving member 231 includes opposite first surface 2315 and second surface 2316 in the radial direction. The positioning slot 2311 is a blind slot, which is recessed from the first surface 2315 of the moving member 231 and does not extend through the second surface 2316 of the moving member 231.

The proximal end of the moving member 231 is further provided with a first flange 2313 that extends along a direction perpendicular to the axial direction away from the first surface 2315 of the moving member 231. A distal end of the first flange 2313 protrudes out from the second surface 2316 of the moving member 231 and defines a through hole 2314 along the axial direction. The inner sheath catheter 21 is inserted in the through hole 2314 to fix the inner sheath catheter 21 to the moving member 231. At this time, moving the operating member 232 along the travelling groove 3211 can drive the moving member 231 to move along the axial direction, in turn driving the inner sheath catheter 21 to move along the axial direction relative to the outer sheath catheter 22, so as to make the support skeleton 11 deform to change its radial size.

Please referring to FIG. 3, FIG. 5 and FIGS. 7-8, the diameter adjustment module 23 further includes at least one elastic member 233 connected to the operating member 232. The first housing 321 is provided with at least one first rack 3212 at a position adjacent to the travelling groove 3211, the first rack 3212 extends along a length direction of the travelling groove 3211, and the operating member 232 is provided with at least one second rack 2323 that can mesh with the first rack 3212. The elastic member 233 is configured for driving the first rack 3212 and the second rack 2323 to mesh with each other. When the first rack 3212 and the second rack 2323 mesh with each other, the operating member 232 is positioned relative to the rear housing 32 in the axial direction. That is, the axial position of the operating member 232 is locked. When the first rack 3212 and the second rack 2323 are disengaged from each other, the operating member 232 is capable of sliding along the travelling groove 3211.

Specifically, the first rack 3212 and the second rack 2323 may be respectively provided on two surfaces of the connecting portion 2321 and the first housing 321 which face to each other. In this embodiment, an inner wall of the first housing 321 adjacent to the travelling groove 3211 is provided with two first racks 3212 which extend along the length direction of the travelling groove 3211. That is, the two first racks 3212 are located at two opposite sides of the travelling groove 3211. A surface of the connecting portion 2321 of the operating member 232 facing to the moving portion 2322 is provided with two second racks 2323 that can mesh with the first racks 3212. The two second racks 2323 are located at two opposite ends of the connecting portion 2321, respectively. For this reason, a width of the connecting portion 2321 of the operating member 232 along a width direction of the travelling groove 3211 (i.e., transverse to the length direction of the travelling groove 3211) is greater than that of the travelling groove 3211. Two sides of each second rack 2323 can mesh with two first racks 3212, respectively. The arrangement of two first racks 3212 and two second racks 2323 can enhance the stability of their cooperation.

Further, the elastic member 233 is held between the operating member 232 and the moving member 231 for driving the operating member 232 away from the moving member 231 along a radial direction. Preferably, a plurality of positioning columns 2312 are provided on a bottom face of the positioning groove 2311 of the moving member 231 and correspond to the elastic members 233 one by one. Each elastic member 233 is mounted around one corresponding positioning column 2312, and the connecting portion 2321 defines a guiding groove 2325 corresponding to the positioning column 2312. When the operating member 232 is pressed radially to move towards the moving member 231, the moving portion 2322 drives the connecting portion 2321 to move radially towards the moving member 231 to compress the elastic member 233, which makes the positioning column 2312 slide in the corresponding guiding groove 2325, the first racks 3212 and the second racks 2323 disengage from each other, and the elastic member 233 is compressed and generates deformation. At this time, the operating member 232 is capable of sliding along the travelling groove 3211 to drive the moving member 231 to move axially, making the inner sheath catheter 21 fixed to the moving member 231 move axially relative to the outer sheath catheter 22. When the pressure on the operating member 232 is released, the connecting portion 2321 moves radially away from the moving member 231 under the elastic resetting force of the elastic member 233, making the first racks 3212 and the second racks 2323 mesh with each other, in turn making the operating member 232 be positioned relative to the rear housing 32 in the axial direction.

In this embodiment, the elastic members 233, the corresponding positioning columns 2312 and the corresponding guiding grooves 2325 are all four in number. In other embodiments, the number of the elastic members 233, the corresponding positioning columns 2312 and the corresponding guiding grooves 2325 may all be one, two or other positive integers greater than one. In this embodiment, the elastic member 233 is a compression spring. In other embodiments, the elastic member 233 may be rubber member, plastic member, metal member or the like with an elastic effect. In this embodiment, the first racks 3212 and the second racks 2323 are both two in number. In other embodiments, the number of the first racks 3212 and second racks 2323 may be one, three or other positive integers greater than one. In other embodiments, the number of the first racks 3212 and the second racks 2323 may be different, as long as there is at least one pair of meshed first rack 3212 and second rack 2323.

In other embodiments, an outer wall of the first housing 321 adjacent to the travelling groove 3211 is provided with at least one first rack 3212 that extends along the length direction of the travelling groove 3211. A side of the moving portion 2322 adjacent to the moving member 231 is provided with at least one second rack 2323 that can mesh with the first rack 3212. The elastic member 233 is connected between the connecting portion 2321 and the moving member 231 for driving the operating member 232 to approach the moving member 231 along the radial direction. For example, the elastic member 233 is a tension spring. When the operating member 232 is pulled away from the moving member 231 along the radial direction, the first rack 3212 and the second rack 2323 disengage from each other. At this time, the operating member 232 is capable of sliding along the travelling groove 3211 to drive the moving member 231 to move axially, making the inner sheath catheter 21 fixed to the moving member 231 move axially relative to the outer sheath catheter 22. When the pulling force on the operating member 232 is released, the operating member 232 approaches the moving member 231 along the radial direction under the elastic resetting force of the elastic member 233, the first rack 3212 and the second rack 2323 mesh with each other, thereby the operating member 232 being positioned relative to the rear housing 32 in the axial direction. The specific connection mean is similar to the above, which will not be described again.

In other embodiments, the positioning groove 2311 may be defined in the operating member 232. In that case, positioning protrusion may be correspondingly provided on the moving member 231, and the connection between the operating member 232 and the moving member 321 is achieved by the engagement of the positioning protrusion in the positioning groove 2311. In addition, the operating member 232 and the moving member 231 may be connected by other means such as snap-fit and etc. In other embodiments, when the axial length of the connecting portion 2321 of the operating member 232 is sufficiently long, the second racks 2323 may be arranged at a position of the connecting portion 2321 corresponding to a lateral side of the travelling groove 3211. Preferably, the second racks 2323 are arranged at positions of the connecting portion 2321 corresponding to the two opposite sides of the travelling groove 3211. Alternatively, the second racks 2323 are still provided at two axial ends of the connecting portion 2321, and the first racks 3212 are provided at two axial ends of the travelling groove 3211. As long as the first racks 3212 and the second racks 2323 can mesh with each other within the moving range of the operating member 232, the axial position of the operating member 232 can be achieved.

Please referring to FIGS. 2-3 and FIGS. 9-11 together, the adjustment assembly 20 further includes a three-way module 24 which is accommodated in the rear housing 32. The proximal end of the outer sheath catheter 22 is connected to the distal end of the three-way module 24, and the inner sheath catheter 21 catheter is movably inserted in the three-way module 24. Specifically, the three-way module 24 includes a hollow main body 241, a sealing layer 242, and a connecting layer 243 arranged in sequence from the distal end to the proximal end. The proximal end of the main body 241 is provided with a protrusion 2414 corresponding to the sealing layer 242, and the connecting layer 243 is provided with a latching slot 2434 matching with the protrusion 2414. The latching slot 2434 and the protrusion 2414 are matched and clamped, so that the protrusion 2414 and the connecting layer 243 both press the sealing layer 242 to fixedly connect the main body 241, the sealing layer 242 and the connecting layer 243 together.

The distal end of the main body 241 is provided with a second flange 2411, which defines a first connecting hole 2412 extending axially therethrough to an inner cavity of the main body 241. The sealing layer 242 and the connecting layer 243 defines a second connecting hole 2421 and a third connecting hole 2431, respectively, corresponding to the first connecting hole 2412. The distal end of the second flange 2411 further defines a connecting groove 2413 which extends along the axial direction and matches with the outer diameter of the outer sheath catheter 22. The connecting groove 2413 is located at the distal end of the first connecting hole 2412 and communicates with the first connecting hole 2412, and a diameter of the connecting groove 2413 is larger than that of the first connection hole 2412.

The proximal end of the outer sheath catheter 22 is inserted in the connecting groove 2413, and thus it is fixedly connected to the distal end of the three-way module 24. The proximal end of the inner sheath catheter 21 which is movably inserted in the outer sheath catheter 22 is inserted in the three-way module 24 by extending through the first connecting hole 2412, the second connecting hole 2421, and the third connecting hole 2431. Preferably, a sealing ring 244 is provided in the second connecting hole 2421 of the sealing layer 242, and the inner sheath catheter 21 in inserted in an inner cavity of the sealing ring 244. The sealing ring 244 is used to seal a gap between the inner sheath catheter 21 and the second connecting hole 2421, so as to ensure the sealing performance between the inner sheath catheter 22 and the three-way module 24. In this embodiment, the inner sheath catheter 21 is fixed to the moving member 231 after extending through the three-way module 24 from its distal end to its proximal end.

Figure 2:
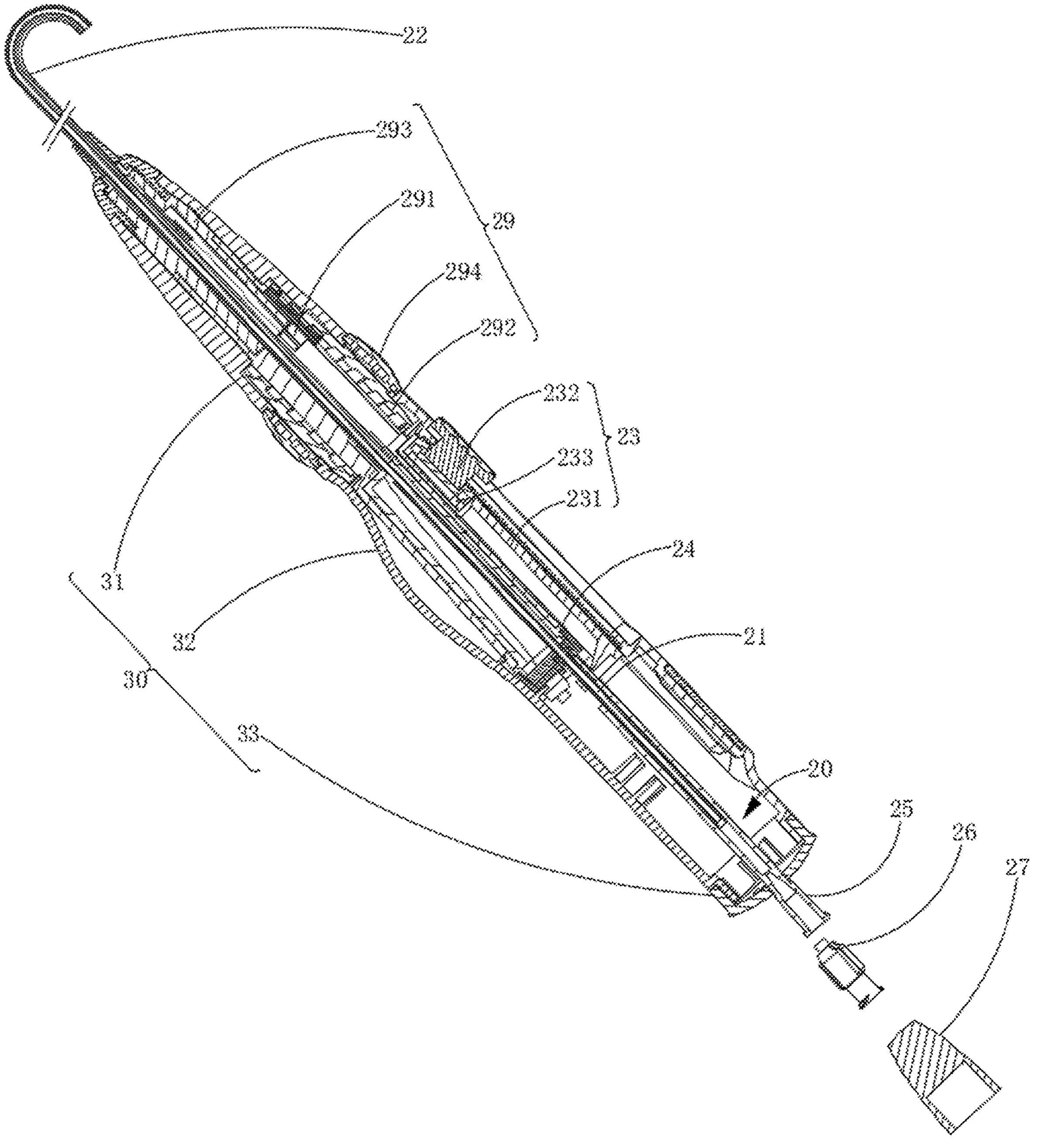
FIG. 2 is a cross-sectional view of an adjustment assembly and a handle of the ablation system of FIG. 1.
Figure 3:
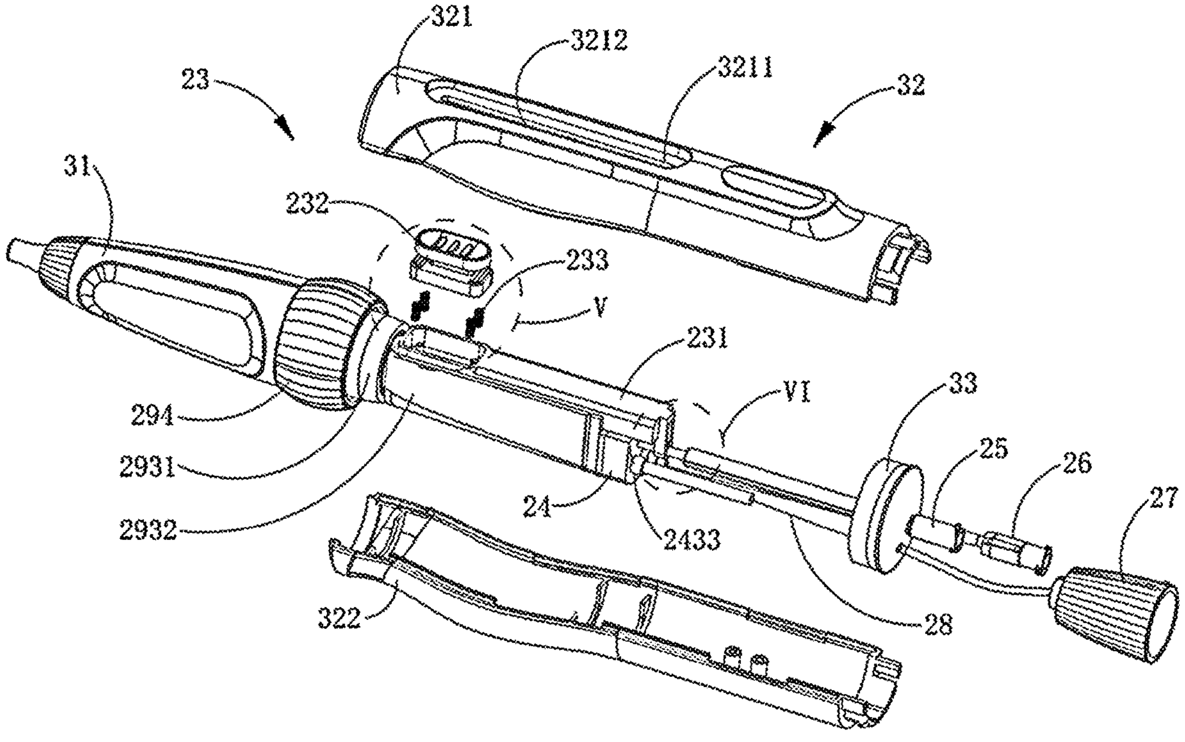
FIG. 3 is a schematic, exploded view of a diameter adjustment module of the adjustment assembly of FIG. 2.
Figure 4:
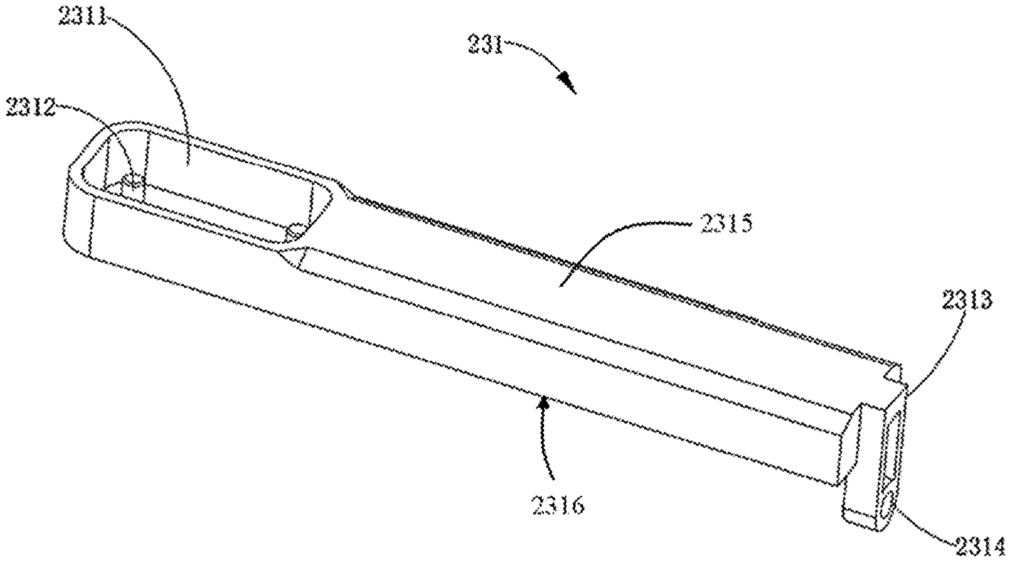
FIG. 4 is a schematic view of a moving member of the diameter adjustment module of FIG. 3.
Figure 5:
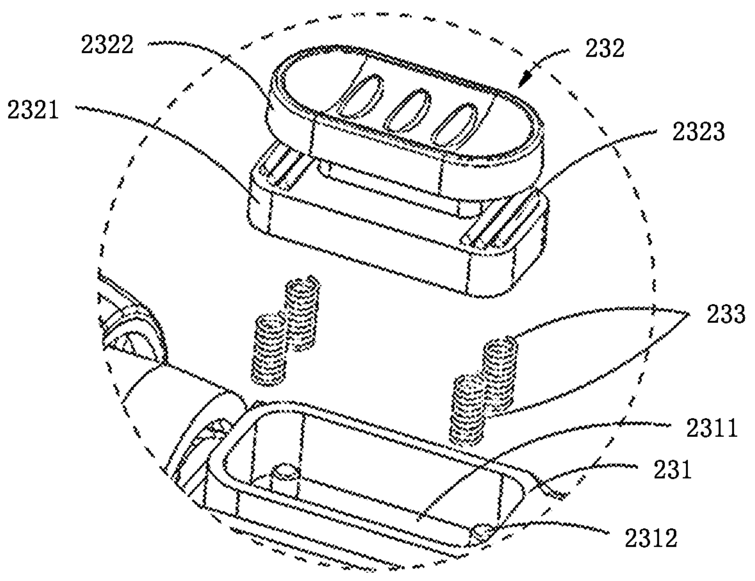
FIG. 5 is an enlarged view of portion V of FIG. 3.
Figure 6:
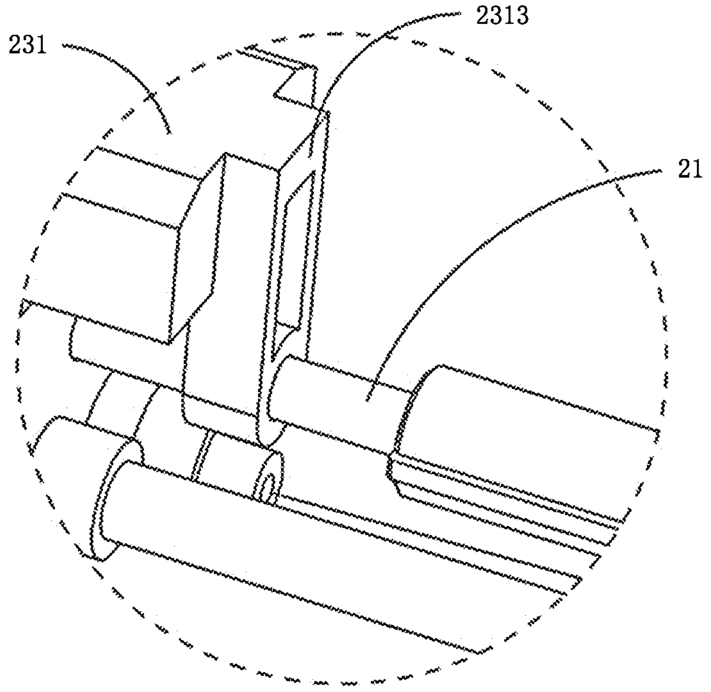
FIG. 6 is an enlarged view of portion VI of FIG. 3.
Figure 7:
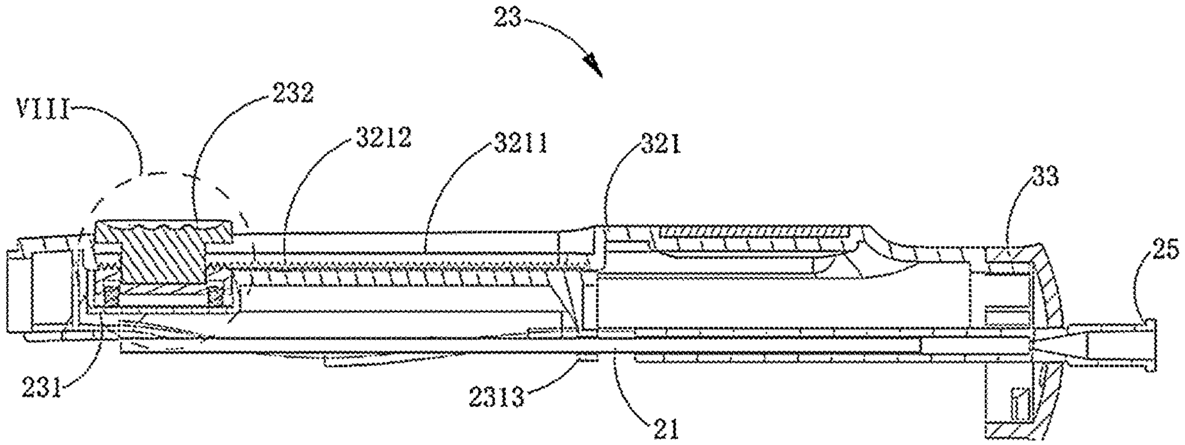
FIG. 7 is a cross-sectional view of the diameter adjustment module of the adjustment assembly of FIG. 2.
Figure 8:
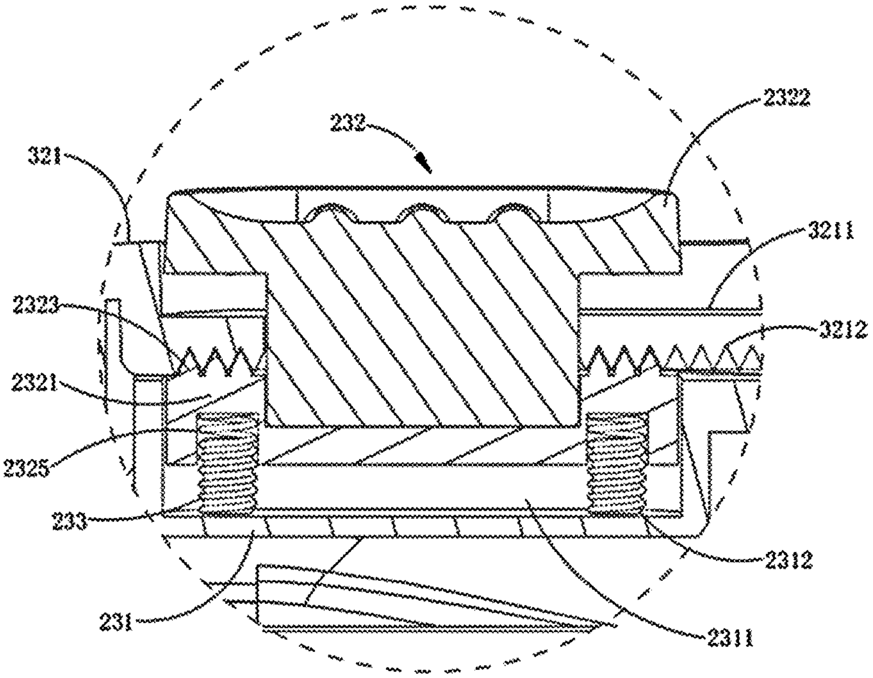
FIG. 8 is an enlarged view of portion VIII of FIG. 7.
Figure 9:
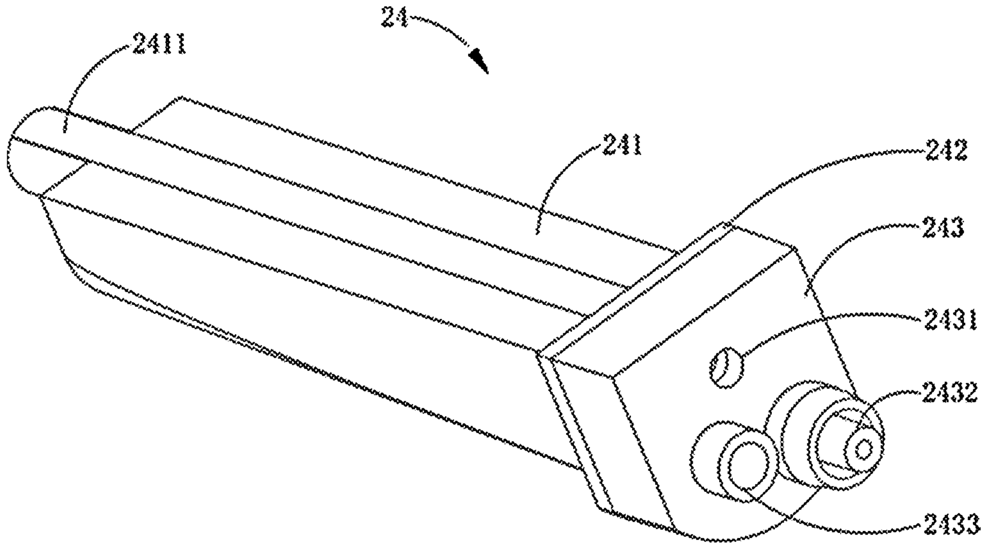
FIG. 9 is a schematic view of a three-way module of the adjustment assembly of FIG. 2.
Figure 10:
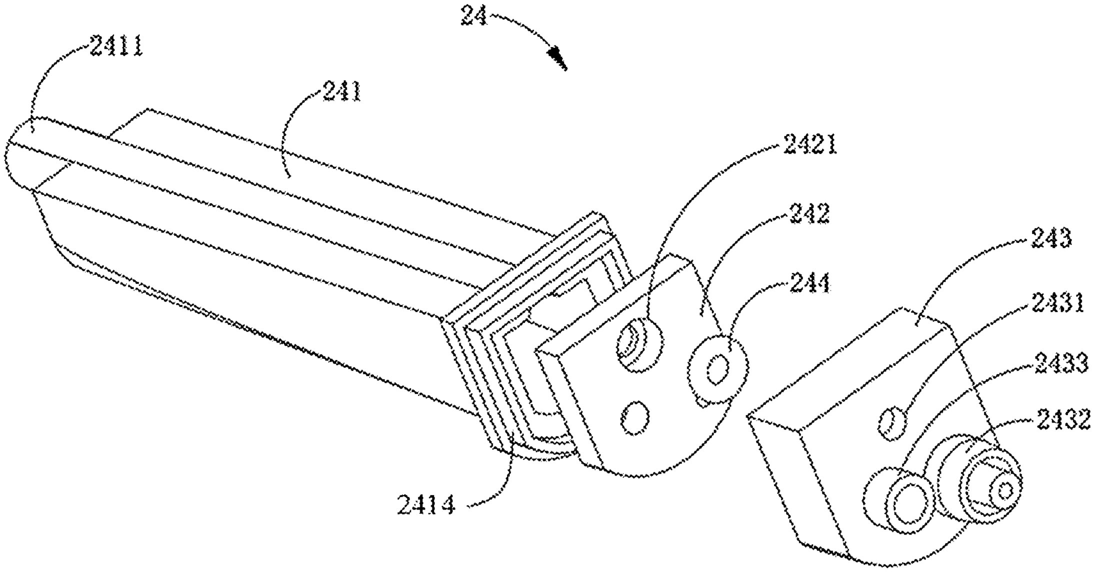
FIG. 10 is a schematic, exploded view of the three-way module of FIG. 9.
Figure 11:
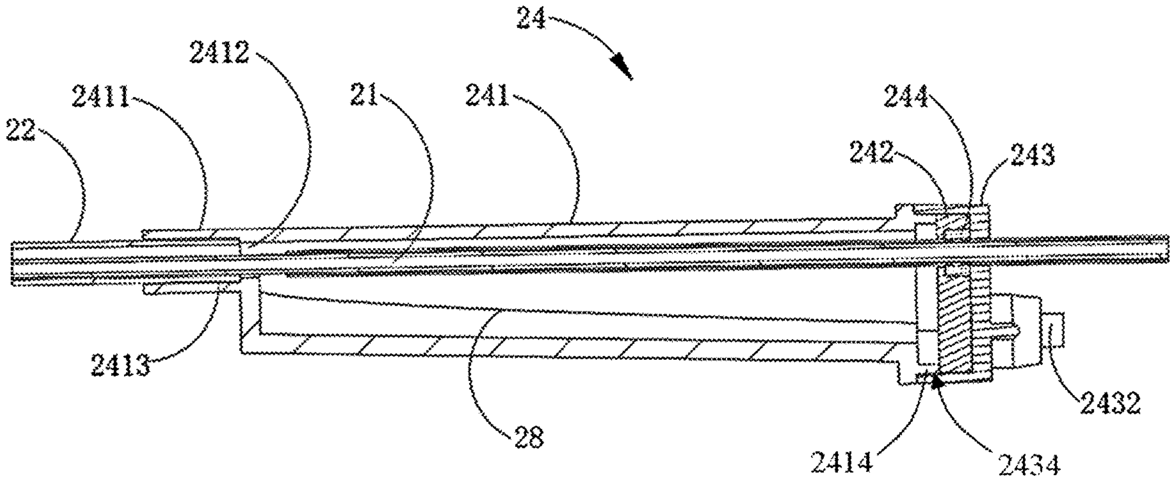
FIG. 11 is a cross-sectional view of a three-way module of the adjustment assembly of FIG. 2.
Figure 12:
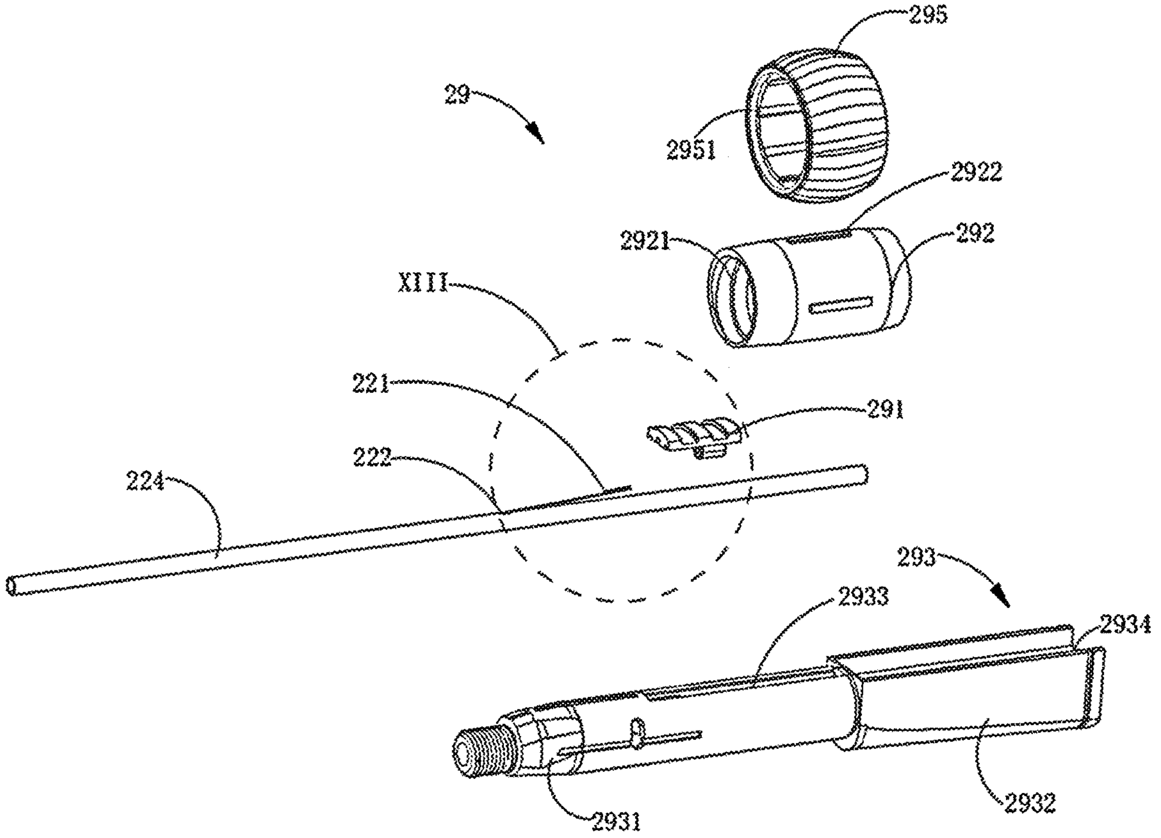
FIG. 12 is exploded view of a bending module of the adjustment assembly of FIG. 2.
Figure 13:
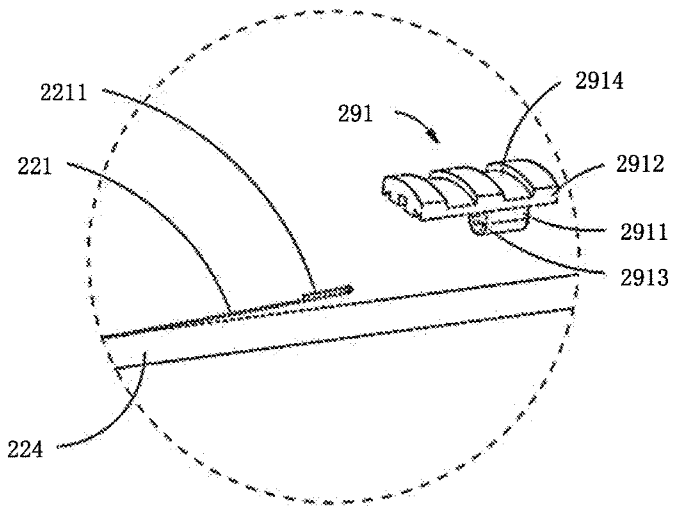
FIG. 13 is a partial, enlarged view of portion XIII of FIG. 12.
Figure 14:
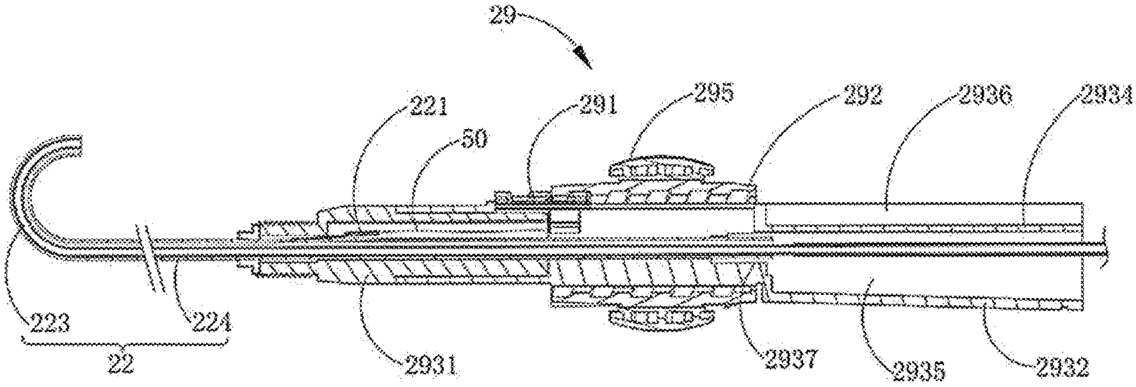
FIG. 14 is a cross-sectional view of the bending module of FIG. 12 after assembly.
Figure 15:
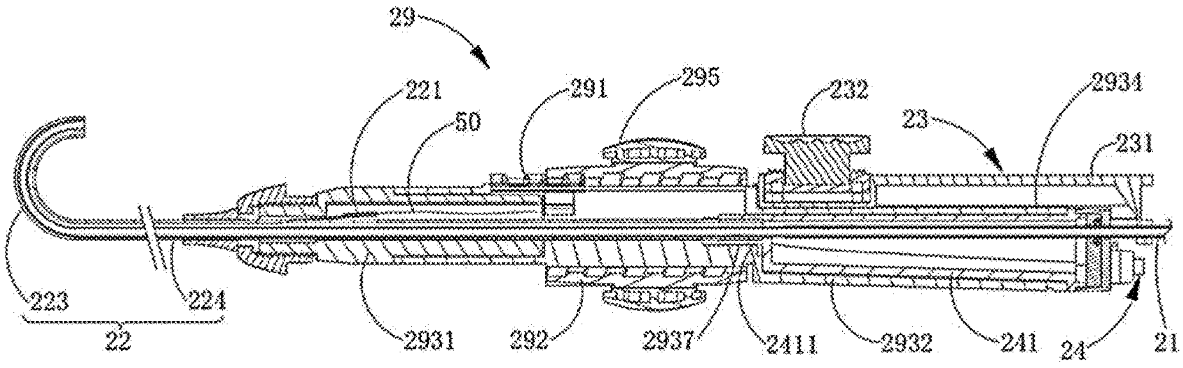
FIG. 15 is a cross-sectional view of the bending module, diameter adjustment module and three-way module of the adjustment assembly of FIG. 2.

Further, please referring to FIG. 2, FIG. 3 and FIG. 7 together, the adjustment assembly 20 further includes a first Luer taper 25 which is inserted in the tail housing 33. The proximal end of the inner sheath catheter 21 is connected to the distal end of the first Luer taper 25 after passing through the moving member 231. The first Luer taper 25 is used to exhaust air from the inner sheath catheter 21, and is in a hollow tubular shape. The proximal end of the inner sheath catheter 21 is inserted in an inner cavity of the first Luer taper 25. Specifically, a step is formed on an inner wall of the inner cavity of the first Luer taper 25, and the distal end of the inner sheath catheter 21 is accommodated in the inner cavity and abuts the step. The step is used for position limit during the fitting of the first Luer taper 25 with the inner sheath catheter 21, so as to improve the connection stability of the first Luer taper 25 and the inner sheath catheter 21. Liquid injected into the first Luer taper 25 all flows along the inner cavity of the first Luer taper 25 into the inner sheath catheter 21, and then flows through the inner sheath catheter 21 and out from the distal end of the inner sheath catheter 21 to exhaust the air in the inner sheath catheter 21, further improving the safety of surgery. Preferably, the liquid may be physiological saline.

Further, please referring to FIG. 2, FIG. 3 and FIGS. 9-11 together, the proximal end of the connecting layer 243 is further provided with a first sealing joint 2432, which extends axially to the inner cavity of the main body 241. The adjustment assembly 20 further includes a second Luer taper 62, which is inserted in the tail housing 33 and is connected to the first sealing joint 2432. Air between the inner sheath catheter 21 and the gap tube can be exhausted by the second Luer taper 62, further improving the safety of the surgery.

It should be noted that the gap tube is in a hollow tubular shape, and located between the inner sheath catheter 21 and the outer sheath catheter 22. The distal end of the gap tube is connected to the distal end of the ablation assembly 10, and the proximal end of the gap tube is fixedly connected to the distal end of the three-way module 24. Liquid injected into the second Luer taper 62 flows along an inner cavity of the second Luer taper 62 into the inner cavity of the three-way module 24 via the first sealing joint 2432. Liquid in the three-way module 24 flows into the gap between the inner sheath catheter 21 and the gap tube via the first connecting hole 2412, and then flows along the gap and out of the distal end of the gap tube to exhaust the air between the inner sheath catheter 21 and the gap tube. It should also be noted that the function of the gap tube is to prevent liquid from contacting wire 28. In this embodiment, the wire 28 may be sandwiched between the outer sheath catheter 22 and the inner sheath catheter 21. If there is no gap tube, the liquid injected from the second Luer taper 62 will flow into the gap between the inner sheath catheter 21 and the outer sheath catheter 22, resulting in direct contact of the liquid and the wire 28.

Further, please referring to FIGS. 1-3 and FIGS. 9-11 together, the proximal end of the connecting layer 243 is further provided with a second sealing joint 2433, which extends axially to the inner cavity of the main body 241. The adjustment assembly 20 further includes a connecting member 27 which is inserted in the tail housing 33 and connected to the second sealing joint 2433. The proximal end of the wire 28 passes through the three-way module 24 from the first connecting hole 2412 along the second sealing joint 2433, and is connected to the connecting member 27. Thus, the wire 28 can be connected to an external energy source (not shown) through the connecting member 27 to transfer energy from the external energy source to the ablation assembly 10, thereby the ablation assembly 10 being capable of ablating tissue.

Preferably, please referring to FIGS. 2-3 and FIGS. 12-14 together, the adjustment assembly 20 further includes a bending module 29. The bending module 29 is accommodated in inner cavities of the front housing 31 and the rear housing 32. The bending module 29 includes a sliding member 291 and a driving member 292 for driving the sliding member 291 to slide along the axial direction. A pulling member 221 is provided on a side wall of the outer sheath catheter 22 with one end thereof connected to the distal end of the outer sheath catheter 22 and the other end thereof connected to the sliding member 291. The sliding member 291 slides along the axial direction to makes the distal end of the outer sheath catheter 22 bend.

In this embodiment, the bending module 29 further includes the main shaft 293, which defines an inner cavity extending axially through its two opposite ends. The outer sheath catheter 22 is inserted in the inner cavity, and defines a wire outlet 222 in the side wall thereof. The pulling member 221 extends out from the wire outlet 222 to connect the sliding member 291.

Specifically, the sliding member 291 includes a first connecting portion 2911 and a second connecting portion 2912. The first connecting portion 2911 defines a connecting hole 2913 for connecting the pulling member 221. The main shaft 293 includes a shaft body 2931 and an accommodating portion 2932 with an inner cavity. The accommodating portion 2932 is arranged at the proximal end of the shaft body 2931 and accommodates the three-way module 24 therein. The shaft body 2931 defines an inner cavity that extends axially through its proximal and distal end faces, and the inner cavity of the shaft body 2931 communicates with the inner cavity of the accommodating portion 2932. That is, the main shaft 293 has an inner cavity that extends through its two opposite ends. The inner cavity of the main shaft 293 is used to receive the proximal end of the outer sheath catheter 22. The shaft body 2931 defines a position limit groove 2933 that extends axially to the accommodating portion 2932. The position limit groove 2933 communicates with the inner cavity of the shaft body 2931, and the first connecting portion 2912 is accommodated in and slidable axially along the position limit groove 2933.

The outer sheath catheter 22 includes a curved section 223 located at the distal end and a main section 224 located at the proximal end. The proximal end of the curved section 223 is connected to the distal end of the main section 224, the proximal end of the main section 224 is inserted in the inner cavity of the main shaft 293, and the wire outlet 222 is defined in a side wall of the main section 224. The pulling member 221 may be a pulling steel wire, and the distal end of the pulling member 221 is fixedly connected to the distal end of the curved section 223. Preferably, the outer wall of the outer sheath catheter 22 may further define a guiding groove extending along its axial direction, and the pulling member 221 may be slidably received in the guiding groove. The proximal end of the pulling member 221 extends out from the wire outlet 222 and then passes through the position limit groove 2933 to connect the first connecting portion 2911.

Specifically, the proximal end of the pulling member 221 is provided with a hook-like structure 2211 connected to the first connecting portion 2911. The hook-like structure 2211 is connected to the connecting hole 2913, that is, the pulling member 221 is connected to the sliding member 291. When the sliding member 291 slides towards the proximal end along the position limit groove 2933, the sliding member 291 can drive the pulling member 221 to move axially towards the proximal end, making the curved section 223 of the outer sheath catheter 22 bend towards the proximal end, which is conducive to position the distal end of the ablation device 100 at the lesion and pointing towards the center of the lesion, ensuring that the ablation device 100 has a better centering effect.

In this embodiment, the hook-like structure 2211 is connected to the connecting hole 2913 through a suture 50. In a modified embodiment, the hook-like structure 2211 may directly hook the connection hole 2913, so as to connect the pulling member 221 to the sliding member 291. Preferably, the flexibility of the curved section 223 of the outer sheath catheter 22 is greater than that of the main section 224. During the movement of pulling member 221 towards the proximal end under the driving of the sliding member 291, the curved section 223 deforms and bends before the main section 224, which is beneficial for adjusting the direction of the axis of the distal end of the ablation device 100, so as to facilitate position of the distal end of the ablation device 100 to the target area.

In this embodiment, the driving member 292 is a rotary cylinder, which is mounted around the shaft body 2931 and located at the distal end of the accommodating portion 2932. When the bending module 29 is accommodated in the front housing 31 and the rear housing 32, two opposite ends of the driving member 292 abut against the proximal end face of the front housing 31 and the distal end face of the rear housing 32, respectively, so that the driving member 292 is fixed to the shaft body 2931 in the axial direction. An inner wall of the driving member 292 is provided with internal threads 2921, and the second connecting portion 2912 of the sliding member 291 is provided with external threads 2914 that mesh with the internal threads 2921. Circumferential rotation of the driving member 292 is able to drive the sliding member 291 to slide axially.

Further, the bending module 29 further includes a rotating member 295 mounted around the driving member 292, and the driving member 292 and the rotating member 295 are fixedly connected by snap-fit. Specifically, a plurality of grooves 2951 which extend along the axial direction and are arranged at intervals along the circumferential direction may be defined in an inner wall of the rotating member 295, and flanges 2922 corresponding to the grooves 2951 of the rotating member 295 one by one may be provided on an outer wall of the driving member 292. The flanges 2922 engage into the corresponding grooves 2951, respectively, so as to fix the rotating member 295 to the driving member 292. Therefore, rotary of the rotating member 295 can drive the driving member 292 to rotate along with it along the circumferential direction, making the driving member 292 drive the sliding member 291 to slide along the axial direction. Preferably, in this embodiment, the flange 2922 is strip-shaped, and its extending direction is consistent with the extending direction of the groove 2951.

It can be understood that in other embodiments, positions of the grooves 2951 and the flanges 2922 may be interchanged, i.e., the flanges 2922 are provided on the inner wall of the rotating member 295, and the grooves 2951 are correspondingly defined in the outer wall of the driving member 292. It is also possible to achieve a fixed connection between the rotating member 295 and the driving member 292 through the cooperation of the grooves 2951 and the flanges 2922.

Preferably, the outer wall of the rotating member 295 is further provided with a plurality of recesses or textures that are beneficial for increasing the friction force between the rotating member 295 and the palm of the hand during rotating of the rotating member 295. In a modified embodiment, the rotating member 295 and the driving member 292 may be formed integrally, or may be fixedly connected together through adhesive bonding, hot melt connection and etc.

Please referring to FIG. 2, FIG. 3, FIG. 9, FIG. 14 and FIG. 15, in this embodiment, the diameter adjustment module 23 is partially positioned out of the main shaft 293, and the three-way module 24 is received in the main shaft 293. Specifically, the accommodating portion 2932 is provided with an interlayer 2934 along the axial direction. The interlayer 2934 divides the inner cavity of the accommodating portion 2932 into a first accommodating space 2935 and a second accommodating space 2936. The second accommodating space 2936 is an area that is not completely enclosed, i.e., a surface of the interlayer 2934 adjacent to the second accommodating space 2936 is exposed. The main shaft 293 defines a fixing groove 2937 at the connection of the shaft body 2931 and the accommodating portion 2932, and the fixing groove 2937 extends axially and intercommunicates the inner cavity of the shaft body 2931 with the first accommodating space 2935. The first accommodating space 2935 matches with the main body 241 of the three-way module 24. When the second flange 2411 of the three-way module 24 engages into the fixing groove 2937, the three-way module 24 is received in the first accommodating space 2935. That is, the three-way module 24 is received in the main shaft 293.

The second accommodating space 2936 matches with the moving member 231, and the moving member 231 is positioned in the second accommodating space 2936, making the diameter adjustment module 23 be positioned in the second accommodating space 2936 and exposed outside the main shaft 293. In one embodiment, the positioning slot 2311 of the moving member 231 may extend through the moving member 231 along the radial direction, and the elastic member 233 is fixed to a bottom wall of the operating member 232 and abuts against a side wall of the main shaft 293, specifically abuts against the interlayer 2934 of the accommodating portion 2932.

Figure 16:
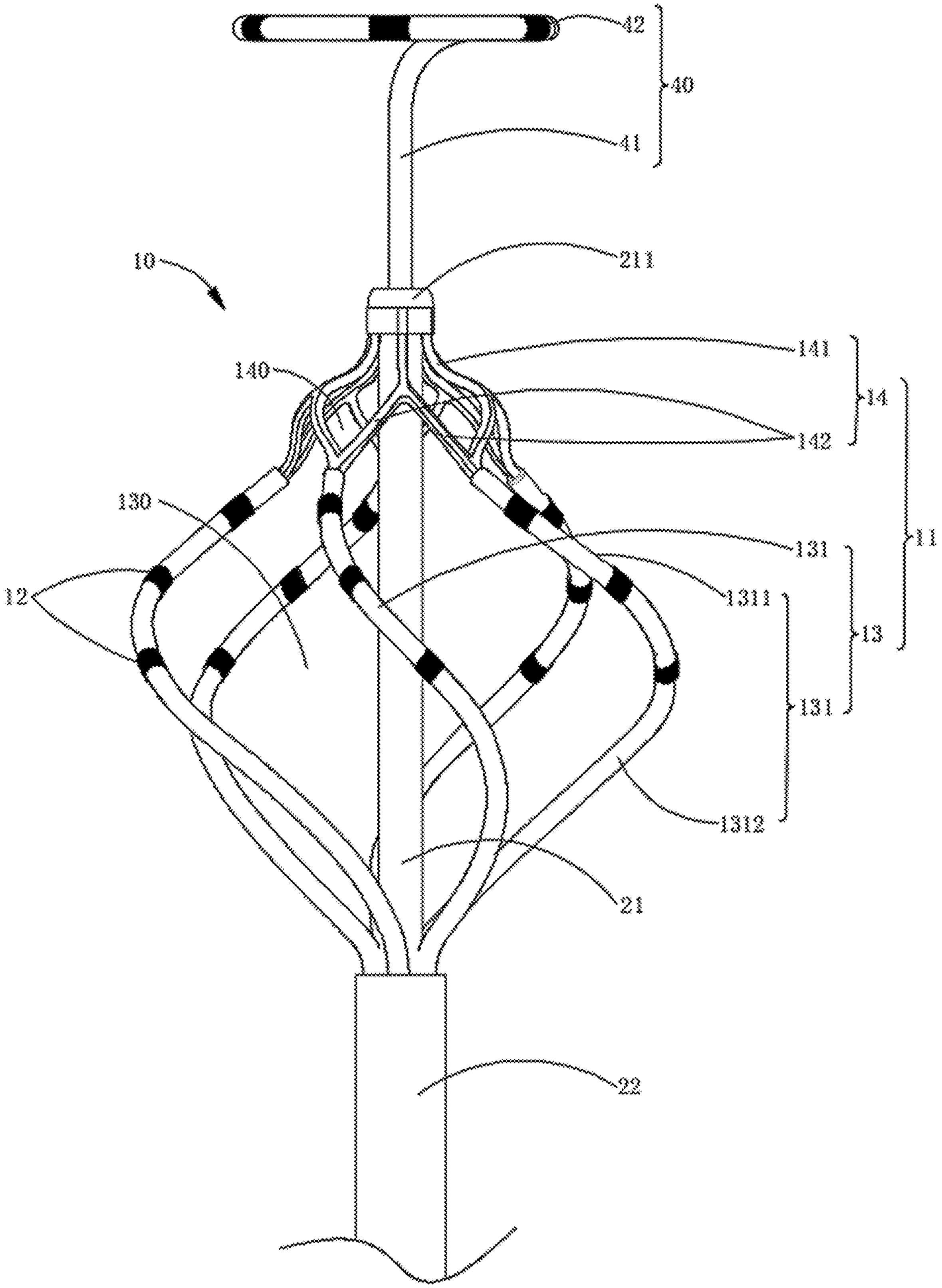
FIG. 16 is a schematic, enlarged view of the ablation assembly, mapping device, and parts of the outer and inner sheath catheters of FIG. 1.
Figure 17:
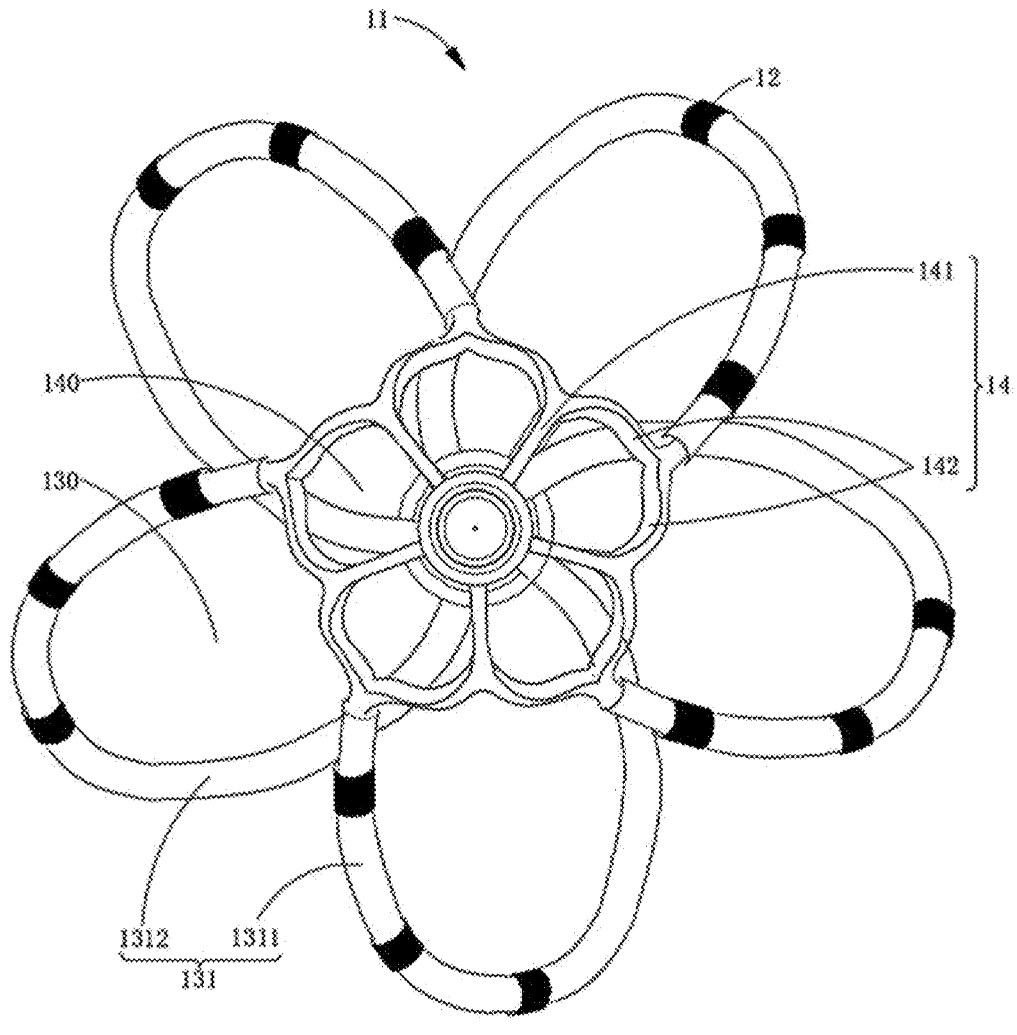
FIG. 17 is a top plan view of the ablation assembly of FIG. 16.
Figure 18:
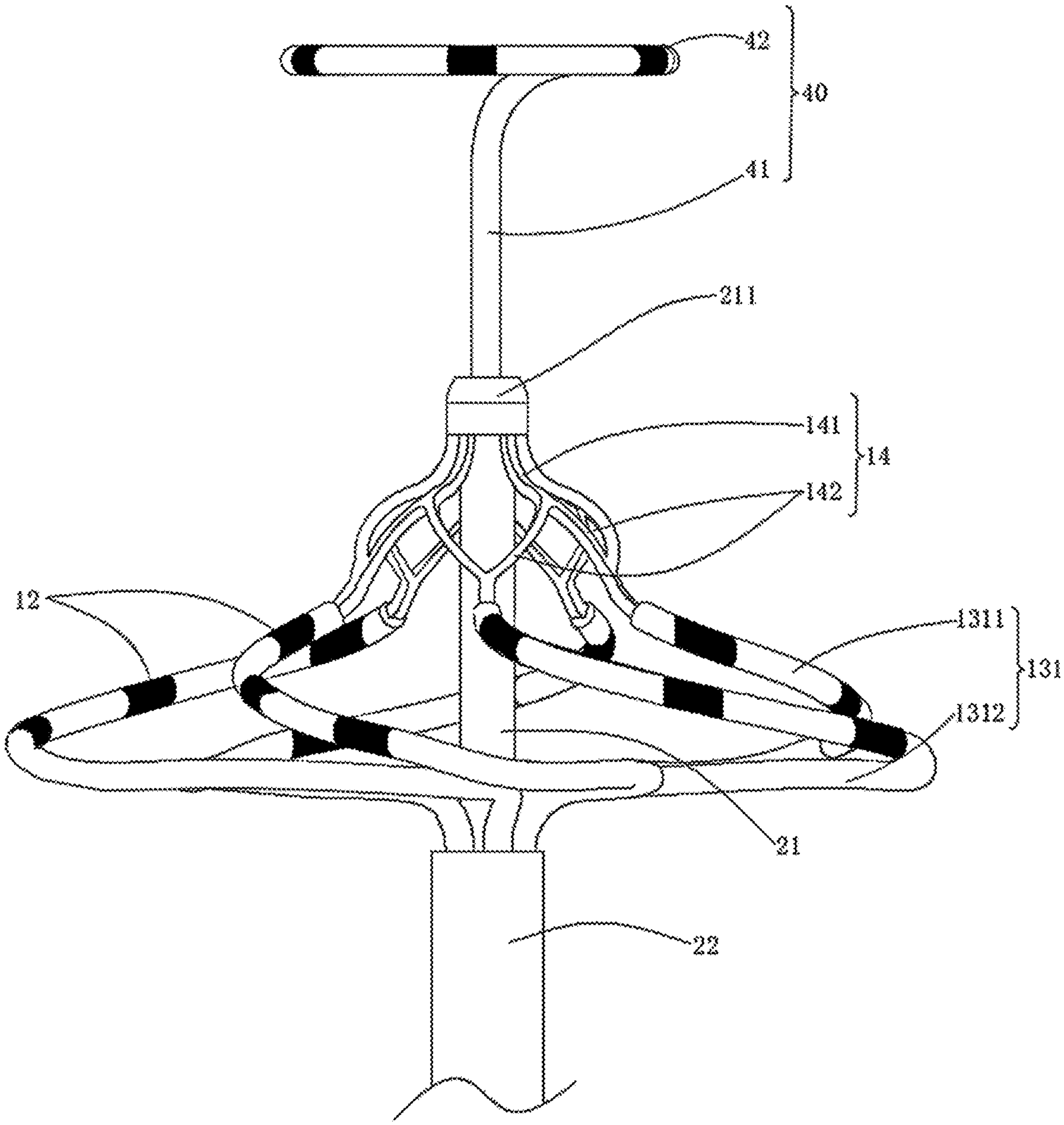
FIG. 18 is a schematic view of one of the usage states of the ablation assembly of FIG. 16.

Please referring to FIGS. 16-18, the support skeleton 11 includes a bearing frame 13 and a positioning frame 14, and the positioning frame 14 is arranged at the distal end relative to the bearing frame 13. The distal end of the outer sheath catheter 22 is connected to the proximal end of the bearing frame 13, and the distal end of the inner sheath catheter 21 is connected to the distal end of the positioning frame 14. When the inner sheath catheter 21 moves axially relative to the outer sheath catheter 22, the support skeleton 11 deforms to change its radial size. Specifically, during the axial movement of the inner sheath catheter 21 toward the proximal end relative to the outer sheath catheter 22, the axial size of the bearing frame 13 decreases and the radial size increases. During the axial movement of the inner sheath catheter 21 towards the distal end relative to the outer sheath catheter 22, the axial size of the bearing frame 13 increases and the radial size decreases.

During the deformation of the support skeleton 11, a deformation ratio of the positioning frame 14 is less than that of the bearing frame 13. The deformation ratio is a ratio of the size of the frame in the fully released state minus the size after deformation to the size in the fully released state. For example, in the axial direction, assume that the size of the frame in the fully released state is L1, the size of the frame after deformation is L2, and the deformation ratio is denoted as A, that is $A=(L1-L2)/L1$.

Specifically, in the axial direction, assume that the size of the positioning frame 14 in the fully released state is M1, the size of the positioning frame 14 after deformation is M2, and the deformation ratio is denoted as A1, that is $A1=(M1-M2)/M1$.

Specifically, in the axial direction, assume that the size of the bearing frame 13 in the fully released state is N1, the size of the bearing frame 13 after deformation is N2, and the deformation ratio is denoted as A2, that is $A2=(N1-N2)/N1$.

The deformation ratio of the positioning frame 22 is less than the deformation ratio of the bearing frame 24, that is $A1<A2$.

In this embodiment, when the support skeleton 11 is in the fully released state, both the positioning frame 14 and the bearing frame 13 are frame structures with inner cavities, the radial size of the positioning frame 14 is less than the radial size of the bearing frame 13, and the axial size of the positioning frame 14 is less than the axial size of the bearing frame 13. In a modified embodiment, the radial size of the positioning frame 14 may be greater than or equal to the radial size of the bearing frame 13, and the axial size of the positioning frame 14 may be greater than or equal to the axial size of the bearing frame 13.

Optionally, both the positioning frame 14 and the bearing frame 13 are grid structures, the positioning frame 14 is formed with a plurality of mesh holes 140, and the bearing frame 13 is formed with a plurality of mesh holes 130. An opening area of the mesh holes 140 in the positioning frame 14 is less than that of the mesh holes 130 in the bearing frame 13, and adjacent gridlines in the grid of the positioning frame 14 are interconnected, making the positioning frame 14 not be easy to deform.

In this embodiment, the support skeleton 11 is made by cutting a nickel-titanium alloy pipe. A cross section of the rod obtained by cutting the positioning frame 14 is the same as that of rod obtained by cutting the bearing frame 13, and the size of the mesh holes 140 is less than that of the mesh holes 130, for example, in this embodiment, both the mesh holes 140 and the mesh holes 130 are elongated and strip-shaped, and the opening area of the mesh holes 140 is less than that of the mesh holes 130 in the fully released state. Due to the grid of the bearing frame 13 is larger than the grid of the positioning frame 14, the deformation ratio of the positioning frame 14 is less than that of the bearing frame 13 during the relative movement between the outer sheath catheter 22 and the inner sheath catheter 21, i.e., during the deformation of the support skeleton 11.

In addition, when the ablation assembly 10 is positioned around the orifice of the pulmonary vein, the bearing frame 13 is easier to deform than the positioning frame 14, which is beneficial for approaching to the target tissue region. The positioning frame 14 has a smaller mesh size, and the gridlines in the positioning frame 14 are interconnected and jointed to each other, which makes the positioning frame 14 have a smaller deformation ratio and be easier to maintain its original shape than the bearing frame 13, thereby maintaining a better centering effect. That is, the ablation assembly 10 is positioned at the orifice of the pulmonary vein, and its axis is easier to align with the center of the pulmonary vein, which avoids large deformation of the positioning frame 14 during the diameter adjustment of the bearing frame 13, which results that the positioning frame 14 cannot press between inner walls of the pulmonary veins, and the ablation assembly 10 fails to align around the orifice of the pulmonary vein. In addition, an outer profile of the positioning frame 14 is not large in deformation ratio and protrudes from the bearing frame 13 in the axial direction, facilitating entering of the ablation assembly 10 into the pulmonary vein, and positioning the bearing frame 13 around the orifice of the pulmonary vein.

Please referring to FIG. 16, specifically, the positioning frame 14 includes a plurality of first main rods 141 and a plurality of first branch rods 142 from the distal end to the proximal end. The plurality of first main rods 141 are arranged along the circumferential direction of the inner sheath catheter 21. The distal end of each first main rod 141 is connected to the inner sheath catheter 21, and the proximal end of each first main rod 141 is connected to multiple corresponding first branch rods 142. The bearing frame 13 includes a plurality of bearing rods 131 arranged along the circumferential direction of the inner sheath catheter 21, and the distal end of each bearing rod 131 is connected to multiple corresponding first branch rods 142. The other ends of the multiple first branch rods 142 connected to the same bearing rod 131 are connected to different first main rods 141, and the proximal end of each bearing rod 131 is connected to the outer sheath catheter 22.

The positioning frame 14 is in a mesh shape and arranged at the distal end of the bearing frame 13. The bearing frame 13 is also in a mesh shape and arranged at the proximal end of the positioning frame 14. The positioning frame 14 is used to insert into the pulmonary vein during the ablation process, with guiding and positioning functions, facilitating the bearing frame 13 to form of an enclosed annular ablation area at the orifice of the pulmonary vein, improving the accuracy of ablation and the success rate of surgery.

In this embodiment, the positioning frame 14 includes five first main rods 141 and two first branch rods 142 connected to the proximal end of each first main rod 141. The plurality of first main rods 141 are arranged along the circumferential direction of the inner sheath catheter 21. Preferably, these first main rods 141 are evenly arranged along the circumferential direction of the inner sheath catheter 21. The bearing frame 13 includes five bearing rods 131 arranged, preferably evenly arranged along the circumferential direction of the inner sheath catheter 21. The distal end of each first main rod 141 is connected to the distal end of the inner sheath catheter 21, and the bearing rod 131 is connected with the first main rod 141 through the first branch rod 142. Specifically, the proximal end of each first main rod 141 is connected to two first branch rods 142, the distal end of each bearing rod 131 is connected to two first branch rods 142, and the distal ends of the two first branch rods 142 connected to the distal end of each bearing rod 131 are connected to neighboring first main rods 141, respectively. Preferably, a fixing member 211 is mounted around the distal end of the inner sheath catheter 21, and the distal end of each first main rod 141 is fixed in an inner wall of the fixing member 211.

In this embodiment, the proximal end of each first main rod 141 is connected to the distal ends of two corresponding first branch rods 142. The proximal ends of the two first branch rods 142 connected to the proximal end of each first main rod 141 extend in directions opposite from each other. The proximal end of each first branch rod 142 is jointed to the proximal end of a neighboring first branch rod 142, that is, the proximal end and distal end of each first branch rod 142 are connected to different first branch rods 142. A joint of the proximal ends of the first branch rods 142 is connected to the distal end of the bearing rod 131, and a joint of the distal ends of the first branch rods 142 is connected to the proximal end of the first main rod 141.

In other words, the plurality of first branch rods 142 are arranged along the circumferential direction of the inner sheath catheter 21, and the first branch rods 142 are connected end to end to form a wave-shaped annular structure. The proximal end of each first main rod 141 is connected to a corresponding peak of the wave-shaped annular structure, and the distal end of each bearing rod 131 is connected to a corresponding trough of the wave-shaped annular structure. In this embodiment, one end of the first branch rod 142 for connecting the bearing rod 131 extends towards the proximal end with respect to one end of the first branch rod 142 for connecting the first main rod 141. In a modified embodiment, one end of the first branch rod 142 for connecting the bearing rod 131 extends towards the distal end with respect to one end of the first branch rod 142 for connecting the first main rod 141, that is, the proximal end of each first main rod 141 is connected to the corresponding trough of the wave-shaped annular structure, and the distal end of each bearing rod 131 is connected to the corresponding peak of the wave-shaped annular structure.

Optionally, the bearing rods 131, the first main rods 141, and the first branch rods 142 may be straight, spiral, or other curved.

In this embodiment, each bearing rod 131 is a spiral rod, and further, a spiral angle range of each bearing rod 131 is between 10 degrees and 70 degrees. The twist angle (i.e., spiral angle) of each bearing rod 131 at different positions from the proximal end may be different. Specifically, the spiral angle of the bearing rod 131 at a position between its proximal and distal ends is greater than the spiral angle of the bearing rod 131 at its proximal end or distal end. That is, the spiral bearing rod 131 has the largest spiral angle at a position between its proximal and distal ends.

In this embodiment, the spiral angle of the bearing rod 131 at a midpoint between its proximal and distal ends is greater than the spiral angle at its proximal or distal ends, and the spiral angle decreases from the midpoint to both sides. In a preferred embodiment, the spiral angles of the bearing rod 131 are symmetrically distributed at two sides of the midpoint. Such spiral distribution structure allows the ablation assembly 10 to have better compliance and can be attached to the ablation tissue area closely. In this embodiment, the overall shape of the spiral bearing rod 131 on a cross-sectional plane passing through the axis is elliptical, circular, or any other geometric shape that is symmetrical. Optionally, the spiral shape of the bearing rod 131 may be obtained by heat setting after cutting. Alternatively, relative rotation between the inner sheath catheter 21 and the outer sheath catheter 22 may be made during the implantation process, so as to form the spiral structure.

Further, the intersection of each first main rod 141 and the multiple corresponding first branch rods 142 is bent towards a side away from the inner sheath catheter 21, the middle of each bearing rod 131 is bent towards a side away from the inner sheath catheter 21, and the intersection of the distal end of each bearing rod 131 and the multiple corresponding first branch rods 142 is bent towards a side close to the inner sheath catheter 21. That is, the intersection of each first main rod 141 and the multiple corresponding first branch rods 142 protrudes away from the inner sheath catheter 21, the middle of each bearing rod 131 protrudes away from the inner sheath catheter 21, and the intersection of the distal end of each bearing rod 131 and the multiple corresponding first branch rods 142 is recessed towards the inner sheath catheter 21, making the bearing frame 13 be easier to deform than the positioning frame 14 during the deformation of the ablation assembly 20.

When the relative positional relationship between the inner sheath catheter 21 and the outer sheath catheter 22 is adjusted to adjust the outer diameter of the bearing frame 24, since two neighboring first main rods 141 are restrained by two first branch rods 142 that are jointed together, the first branch rods 142 pull the first main rod 141 in the axial and radial directions, so that the radial and axial deformation of the first main rod 141 is not too large, which is conducive to maintain the basket-like shape of the positioning frame 14. Thus, during the process of changing the ablation diameter range of the ablation device 100, a better centering effect is maintained, and the problem of large deformation of the positioning frame 14 during diameter adjustment of the bearing frame 13 and failure to press the inner walls of the pulmonary vein, which causes the ablation assembly 10 to be unable to align around the orifice of the pulmonary vein, is avoided.

In a modified embodiment, the proximal end of one first main rod 141 may be connected to more than two first branch rods 142. In this embodiment, the widths of the first main rod 141 and/or the first branch rod 142 are less than or equal to the width of the bearing rod 131, thereby facilitating delivery in the human body by retracting it into a sheath catheter with a smaller diameter. In this embodiment, when the support skeleton 11 is in the fully released state, a radial size of a frame formed by the plurality of first main rods 141 and first branch rods 142 is less than that of a frame formed by the plurality of bearing rods 131.

Please referring to FIGS. 16-18, at least one ablation member 12 is provided on the bearing frame 13 of the support skeleton 11. Specifically, the ablation member 12 may be an ablation electrode. At least one of the bearing rods 131 of the bearing frame 13 is provided with at least one ablation electrode. Specifically, it may be that one of the bearing rods 131 of the bearing frame 13 is provided with ablation electrodes, or each of the bearing rods 131 is provided with ablation electrodes. Further, it may be that several spaced or neighboring bearing rods 131 are provided with ablation electrodes. Optionally, the number of the ablation electrodes on different bearing rods 131 may be the same with or different from each other. Preferably, the bearing rods 131 each are provided with the same number of ablation electrodes. Optionally, the ablation energy source connected to the ablation member 12 may be radio frequency, pulse, or microwave. Preferably, the ablation energy source connected to the ablation member 12 is a pulse.

The ablation member 12 may be arranged on either side face of the bearing rod 131, for example, on a side face away from the inner sheath catheter 12. In addition, the ablation member 12 may be mounted around the whole outer circumferential wall of the bearing rod 131. Specifically, each bearing rod 131 includes a bearing section 1311 arranged adjacent to its distal end and a connecting section 1312 arranged adjacent to its proximal end, and the ablation members 12 are arranged in the bearing section 1311. In this embodiment, each bearing section 1311 is provided with three ablation members 12, which are spaced from each other along the axial direction of the bearing section 1311 and mounted around the outer circumferential wall of the bearing section 1311. The ablation members 12 are arranged in the bearing section 1311 which is adjacent to the distal end of the bearing rod 131, ensuring that the distance between the multiple ablation members 12 is not too close during ablation of the orifice of the pulmonary vein, i.e., during the deformation of the support skeleton 11, thereby avoiding the generation of electric arcs, and at the same time ensuring that the ablation members 12 of the ablation assembly 10 can be well attached to and compliant with the atrial tissue. Preferably, the shape of the ablation member 12 conforms to the spiral shape of the bearing rod 131.

In some embodiments, the ablation member 12 may be provided at the middle of the bearing rod 131, that is, at the connection point of the bearing section 1311 and the connecting section 1312. In another embodiment, the ablation member 12 may be provided on the connecting section 1312. Optionally, the ablation member 12 may be provided on the proximal end of the connecting section 1312. Preferably, the number of the ablation members 12 provided on the connecting section 1312 is less than that provided on the bearing section 1312. When the bearing frame 13 is compressed and deformed, it is beneficial to avoid short circuits caused by contact of the ablation members 12 on the two neighboring bearing rods 131.

In some embodiments, at least one of the bearing rods 131 is provided with an ablation member 12 at a position thereof farthest from its axis. In this embodiment, the bearing rod 131 is a spiral rod, and the spiral angle of the bearing rod 131 at a midpoint between the proximal and distal ends is greater than that at the proximal end or the distal end of the bearing rod 131. Moreover, the spiral angle decreases from the midpoint to both sides, and the middle of the bearing rod 131 protrudes away from the inner sheath catheter 21. That is, the midpoint of the bearing rod 131 is the position farthest from the axis of the inner sheath catheter 21, the position farthest from its axis, the position of the support frame 11 with the largest diameter, and the convex position of the bearing rod 131. The ablation member 12 is arranged at the convex position. When the ablation assembly 10 is ablated inside the pulmonary vein, the ablation member 12 at the convex position can better approach to the inner wall tissue of the pulmonary vein, which facilitates ablation. In other embodiments, the convex position of the bearing rod 131 is not coincide with the midpoint of the bearing rod 131.

In this embodiment, each of the bearing rods 131 is provided with the ablation members, which are ablation electrodes. The polarities of the ablation electrodes on each bearing rod 131 are the same, while the polarities of two neighboring ablation electrodes on neighboring bearing rods 131 are opposite. That is, the ablation electrodes on each bearing rod 131 may be electrically connected to the external energy source through one wire. In a modified embodiment, each ablation electrode may be electrically connected to the external energy source through one wire, enabling independent addressing of each ablation electrode. In a modified embodiment, the polarities of two neighboring ablation electrodes on the same bearing rod 131 are opposite, and the polarities of two neighboring ablation electrodes on neighboring bearing rods 131 are opposite.

When the ablation device 100 is in use, the ablation members 12 on the bearing rods 131 are configured for annular ablation, such as at the orifice of the pulmonary vein. The inner sheath catheter 21 of the adjustment assembly 20 is movably inserted in the outer sheath catheter 22, the distal end of the inner sheath catheter 21 can extend out from the distal opening end of the outer sheath catheter 22 and joint to the distal end of the positioning frame 14, and the proximal end of the bearing frame 13 is jointed to the distal end of the outer sheath catheter 22. By means of the relative positional relationship between the inner sheath catheter 21 and the outer sheath catheter 22, the axial length of the bearing frame 13 is controlled to adjust the diameter of the bearing frame 13, so that the diameter of the bearing frame 13 matches with the annular size of the target ablation region.

Optionally, in other embodiments, the positioning frame 14 is provided with the ablation members 12, and the bearing frame 13 is not provided with the ablation member 12. Specifically, the ablation members 12 are provided on the first main rod 141 and/or the first branch rod 142 of the positioning frame 14, and the setting of the ablation members 12 refers to that on the bearing frame 13, which will not be described again. In other embodiments, both the positioning frame 14 and the bearing frame 13 may be provided with the ablation members 12.

Optionally, please referring to FIG. 1, FIGS. 3 and 16, the mapping device 40 includes a mapping catheter 41 and a mapping member 42 arranged at the distal end of the mapping catheter 41. The mapping member 42 may be a mapping electrode. The mapping catheter 41 is inserted in the inner sheath catheter 21. The mapping member 42 extends out from the distal end of the inner sheath catheter 21 to contact the tissue wall for detecting the electrophysiological signals in the target tissue region. Specifically, the distal end of the mapping catheter 41 extends spirally for at least one circle after extending out the distal end of the inner sheath catheter 21, and several mapping members 42 are arranged at the distal end of the mapping catheter 41 and spaced from each other. The mapping catheter 41 is inserted in the inner sheath catheter 21, and the mapping member 42 extends out from the distal opening end of the inner sheath catheter 21 to contact the tissue wall for detecting electrophysiological signals in the target tissue region.

In other embodiments, the ablation member 12 on the support skeleton 11 can be used not only for ablation, but also for contacting the tissue wall to detect electrophysiological signals in the target tissue region. If the ablation member 12 on the bearing frame 13 can be used for detecting electrophysiological signals in the target tissue region, the mapping device 40 can be omitted accordingly.

The following describes the use process of the ablation device 100 provided by the present invention according to the process of forming at least one enclosed annular ablation region around the orifice of the pulmonary vein by the ablation system and the ablation device 100 to treat arrhythmia.

Step 1: please referring to FIG. 1, FIG. 2 and FIGS. 15-18, physiological saline is injected into the inner sheath catheter 21 through the first Luer taper 25, and flows along the inner cavity of the first Luer taper 25 into the inner sheath catheter 21, and flows in the inner sheath catheter 21 and out from the distal end of the inner sheath catheter 21 to exhaust air in the inner sheath catheter 21; air between the inner sheath catheter 21 and the gap tube is exhausted by the second Luer taper 26.

Step 2: the distal end of the ablation system 100 is positioned around the orifice of the pulmonary vein, the rotating member 294 of the bending module 29 is rotated to bend the distal end of the outer sheath catheter 21 to adjust the orientation of the axis of the ablation assembly 10 at the distal end; the rotating member 294 is rotated until the mapping member 42 of the mapping device 40 contacting the tissue wall to detect electrophysiological signals in the orifice of the pulmonary vein orifice, and the ablation assembly 10 at the distal end is delivered to the center of the orifice of the pulmonary vein.

Step 3: the operating member 232 of the diameter adjustment module 23 slides towards the proximal end, the inner sheath catheter 21 moves relative to the outer sheath catheter 22 towards the proximal end to make the bearing frame 13 of the support skeleton 11 compress and deform to form an annular structure; the ablation member 12 provided on the bearing frame 13 ablates the tissue around the orifice of the pulmonary vein during or after the compression and deformation of the bearing frame 13, forming at least one enclosed annular ablation region, thereby finishing the treatment.

It should be understand that the ablation system and ablation device 100 of this embodiment may also be applied to other lesions such as the aorta and etc., so as to treat arrhythmia.

The above is embodiments of the present invention, and it should be pointed out that some modifications and embellishments can be made without departing from the principles of the embodiments of the present invention for persons of ordinary skill in the art. These modifications and embellishments are also considered to be within the scope of the present invention.

What is claimed is:

1. An ablation device, comprising an ablation assembly and an adjustment assembly provided at the proximal end of the ablation assembly, the ablation assembly comprising a support skeleton and an ablation member provided on the support skeleton;

the adjustment assembly comprising an inner sheath catheter, an outer sheath catheter and a diameter adjustment module, the inner sheath catheter being movably mounted in the outer sheath catheter along an axial direction, the distal end of the outer sheath catheter being connected to the proximal end of the support skeleton, the distal end of the inner sheath catheter being connected to the distal end of the support skeleton, the inner sheath catheter being connected to the diameter adjustment module, the diameter adjustment module being movable along the axial direction to drive the inner sheath catheter to move relative to the outer sheath catheter along the axial direction, so as to make the support skeleton deform to change a radial size thereof;

wherein the adjustment assembly further comprises a bending module, the bending module comprises a sliding member and a driving member, a pulling member is provided on a side wall of the outer sheath catheter with one end thereof connected to the distal end of the outer sheath catheter and the other end thereof connected to the sliding member, and the driving member is configured for driving the sliding member to slide along the axial direction, so as to bend the distal end of the outer sheath catheter;

wherein the bending module further comprises a main shaft with an inner cavity extending axially through two opposite ends thereof, the outer sheath catheter is inserted in the inner cavity and defines a wire outlet in the side wall thereof, and the pulling member extends out via the wire outlet to connect the sliding member;

wherein the outer sheath catheter comprises a curved section and a main section connected to the proximal end of the curved section, the main section is inserted in the inner cavity of the main shaft, the wire outlet is defined in a side wall of the main section, the one end of the pulling member is fixedly connected to the distal end of the curved section, and the other end of the pulling member extends out via the wire outlet to connect the sliding member; and wherein the main shaft defines a position limit groove along the axial direction, the sliding member is slidably accommodated in the position limit groove, the inner cavity of the main shaft communicates with the position limit groove, and the pulling member extends out via the wire outlet and the position limit groove to connect the sliding member, wherein the driving member is mounted around the main shaft, an inner wall of the driving member is provided with internal threads, the sliding member is provided with external threads that mesh with the internal threads, and the driving member rotates along a circumferential direction to drive the sliding member to slide along the position limit groove.

2. The ablation device according to claim 1, wherein the diameter adjustment module comprises a moving member and an operating member connected to the moving member, the proximal end of the inner sheath catheter is fixed to the moving member, and the operating member is capable of being moved to drive the moving member to move along the axial direction, so as to make the inner sheath catheter move along the axial direction.

3. The ablation device according to claim 2, further comprising a hollow handle, the moving member being arranged in an inner cavity of the handle, a side wall of the handle defining a travelling groove which extends therethrough to the inner cavity, the travelling groove extending along the axial direction, and the operating member being inserted in the travelling groove.

4. The ablation device according to claim 3, wherein the diameter adjustment module further comprises at least one elastic member connected to the operating member, at least one first rack and at least one second rack that are capable of meshing with each other are provided on surfaces of the handle and the operating member that face to each other along a radial direction; the elastic member makes the first rack and the second rack mesh with each other to lock the operating member relative to the handle in the axial direction, and the operating member is capable of sliding along the travelling groove when the first rack and the second rack are disengaged from each other.

5. The ablation device according to claim 4, wherein the operating member comprises a connecting portion and a moving portion, the connecting portion is received in the inner cavity of the handle, and the moving portion is inserted in the travelling groove and connected to the connecting portion, wherein the distal end of the moving member defines a positioning slot, and the connecting portion is at least partially accommodated in the positioning slot.

6. The ablation device according to claim 5, wherein the at least one first rack comprises two first racks, the at least one second rack comprises two second racks, the two first racks are respectively arranged at two sides of the travelling groove and extend along a length direction of the travelling groove, the two second racks are respectively arranged at two axial ends of a surface of the connecting portion facing to the moving portion, and a width of the connecting portion is greater than that of the travelling groove in a width direction of the travelling groove.

7. The ablation device according to claim 6, wherein the elastic member is connected between the moving member and the connecting portion for driving the operating member away from the moving member along the radial direction, wherein a positioning column is provided at a bottom face of the positioning slot of the moving member corresponding to the elastic member one by one, the elastic member is mounted around the positioning column, the connecting portion defines a guiding groove corresponding to the positioning column, the positioning column is capable of sliding in the guiding groove, and the elastic member is compressed when the operating member is pressed to move towards the moving member.

8. The ablation device according to claim 2, wherein the moving member comprises opposing first and second surfaces, a first flange is arranged at the proximal end of the moving member and extends away from the first surface, a tail end of the first flange protrudes out from the second surface of the moving member and defines a through hole therein, and the inner sheath catheter is fixed to the through hole and is capable of moving along with the moving member.

9. The ablation device according to claim 3, wherein the adjustment assembly further comprises a three-way module received in the inner cavity of the handle, the proximal end of the outer sheath catheter is connected to the distal end of the three-way module, the inner sheath catheter is movably inserted in the three-way module, and the inner sheath catheter is fixed to the moving member after extending through the three-way module from its distal end to its proximal end.

10. The ablation device according to claim 1, wherein the support skeleton comprises a bearing frame and a positioning frame, the positioning frame is arranged at a distal end relative to the bearing frame, the distal end of the outer sheath catheter is connected to the proximal end of the bearing frame, and the distal end of the inner sheath catheter is connected to the distal end of the positioning frame, a deformation ratio of the positioning frame being less than that of the bearing frame during deformation of the support skeleton.

11. The ablation device according to claim 10, wherein at least one of the bearing frame and the positioning frame is provided with at least one ablation member, and the ablation member is ablation electrode, wherein the bearing frame is provided with the ablation electrode, the bearing frame comprises a plurality of bearing rods arranged along the circumferential direction of the inner sheath catheter, the bearing rod comprises a bearing section arranged adjacent to its distal end, and the ablation electrode is arranged in the bearing section.

12. The ablation device according to claim 11, wherein the bearing rod further comprises a connecting section arranged adjacent to its proximal end, and a connection position of the connecting section and the bearing section is provided with the ablation electrode, wherein at least one of the bearing rods is provided with the ablation electrode at a position thereof farthest from the axis of the support skeleton, wherein the ablation electrode is connected to an external pulsed energy source to ablate the target tissue region, each of the bearing rods is provided with a plurality of ablation electrodes along its axial direction, among the plurality of bearing rods, the ablation electrodes correspond one to one along the axial direction, and are arranged around the axis of the support skeleton and at intervals along the circumferential direction.

13. The ablation device according to claim 12, further comprising one of the following features:

- the polarities of the ablation electrodes on each of the bearing rods being the same, and the polarities of neighboring ablation electrodes on two neighboring bearing rods being opposite;
- the polarities of two neighboring ablation electrodes on the same bearing rod being opposite, and the polarities of neighboring ablation electrodes on two neighboring bearing rods being opposite; and
- the polarities of two neighboring ablation electrodes on the same bearing rod being opposite, and the polarities of neighboring ablation electrodes on two neighboring bearing rods being the same.

14. The ablation device according to claim 13, wherein each of the bearing rods is a spiral rod with a spiral angle of 10° to 70°, wherein the spiral angle of the bearing rod at a midpoint between the proximal and distal ends is greater than the spiral angle of the bearing rod at its proximal end or distal end, wherein the spiral angles of the bearing rod are symmetrically distributed about the midpoint of the bearing rod.

15. The ablation device according to claim 1, wherein the ablation member is further configured to contact a tissue wall for detecting electrophysiological signals in the target tissue region.

16. An ablation system, comprising a mapping device and the ablation device according to claim 1, the mapping device comprising a mapping catheter and a mapping member provided at the distal end of the mapping catheter, the mapping catheter being inserted in the inner sheath catheter, and the mapping member extending out from the distal end of the inner sheath catheter to contact a tissue wall for detecting electrophysiological signals in the target tissue region.

17. An ablation device, comprising an ablation assembly and an adjustment assembly provided at the proximal end of the ablation assembly, the ablation assembly comprising a support skeleton and an ablation member provided on the support skeleton;

the adjustment assembly comprising an inner sheath catheter, an outer sheath catheter and a diameter adjustment module, the inner sheath catheter being movably mounted in the outer sheath catheter along an axial direction, the distal end of the outer sheath catheter being connected to the proximal end of the support skeleton, the distal end of the inner sheath catheter being connected to the distal end of the support skeleton, the inner sheath catheter being connected to the diameter adjustment module, the diameter adjustment module being movable along the axial direction to drive the inner sheath catheter to move relative to the outer sheath catheter along the axial direction, so as to make the support skeleton deform to change a radial size thereof;

wherein the diameter adjustment module comprises a moving member and an operating member connected to the moving member, the proximal end of the inner sheath catheter is fixed to the moving member, and the operating member is capable of being moved to drive the moving member to move along the axial direction, so as to make the inner sheath catheter move along the axial direction;

wherein the moving member being arranged in an inner cavity of a hollow handle, a side wall of the handle defines a travelling groove which extends therethrough to the inner cavity, the travelling groove extends along the axial direction, and the operating member is inserted in the travelling groove;

wherein the diameter adjustment module further comprises at least one elastic member connected to the operating member, at least one first rack and at least one second rack that are capable of meshing with each other are provided on surfaces of the handle and the operating member that face to each other along a radial direction; the elastic member makes the first rack and the second rack mesh with each other to lock the operating member relative to the handle in the axial direction, and the operating member is capable of sliding along the travelling groove when the first rack and the second rack are disengaged from each other;

wherein the operating member comprises a connecting portion and a moving portion, the connecting portion is received in the inner cavity of the handle, and the moving portion is inserted in the travelling groove and connected to the connecting portion, wherein the distal end of the moving member defines a positioning slot, and the connecting portion is at least partially accommodated in the positioning slot;

wherein the at least one first rack comprises two first racks, the at least one second rack comprises two second racks, the two first racks are respectively arranged at two sides of the travelling groove and extend along a length direction of the travelling groove, the two second racks are respectively arranged at two axial ends of a surface of the connecting portion facing to the moving portion, and a width of the connecting portion is greater than that of the travelling groove in a width direction of the travelling groove; and wherein the elastic member is connected between the moving member and the connecting portion for driving the operating member away from the moving member along the radial direction, wherein a positioning column is provided at a bottom face of the positioning slot of the moving member corresponding to the elastic member one by one, the elastic member is mounted around the positioning column, the connecting portion defines a guiding groove corresponding to the positioning column, the positioning column is capable of sliding in the guiding groove, and the elastic member is compressed when the operating member is pressed to move towards the moving member.

18. An ablation device, comprising an ablation assembly and an adjustment assembly provided at the proximal end of the ablation assembly, the ablation assembly comprising a support skeleton and an ablation member provided on the support skeleton;

the adjustment assembly comprising an inner sheath catheter, an outer sheath catheter and a diameter adjustment module, the inner sheath catheter being movably mounted in the outer sheath catheter along an axial direction, the distal end of the outer sheath catheter being connected to the proximal end of the support skeleton, the distal end of the inner sheath catheter being connected to the distal end of the support skeleton, the inner sheath catheter being connected to the diameter adjustment module, the diameter adjustment module being movable along the axial direction to drive the inner sheath catheter to move relative to the outer sheath catheter along the axial direction, so as to make the support skeleton deform to change a radial size thereof;

wherein the adjustment assembly further comprises a bending module that comprises a main shaft with an inner cavity extending axially through two opposite ends thereof, a sliding member and a driving member, the main shaft defines a position limit groove extending along an axial direction and communicating with the inner cavity of the main shaft, the sliding member is slidably accommodated in the position limit groove, the driving member is mounted around the main shaft, an inner wall of the driving member is provided with internal threads, the sliding member is provided with external threads that mesh with the internal threads, and the driving member rotates along a circumferential direction to drive the sliding member to slide along the position limit groove.

19. The ablation device according to claim 18, wherein the outer sheath catheter comprises a curved section and a main section connected to the proximal end of the curved section, the main section is inserted in the inner cavity of the main shaft, a wire outlet is defined in a side wall of the main section;

a pulling member is provided on a side wall of the outer sheath catheter with one end thereof connected to the distal end of the curved section of the outer sheath catheter and another end thereof extending out via the wire outlet and the position limit groove to connect the sliding member.

20. The ablation device according to claim 18, wherein the diameter adjustment module comprises a moving member, an operating member connected to the moving member, and at least one elastic member, the moving member is arranged in an inner cavity of a hollow handle, a distal end of the moving member defines a positioning slot;

the operating member comprises a connecting portion and a moving portion, the connecting portion is received in the inner cavity of the handle;

the elastic member is connected between the moving member and the connecting portion for driving the operating member away from the moving member along the radial direction;

at least one first rack and at least one second rack that are capable of meshing with each other are provided on surfaces of the handle and the operating member that face to each other along a radial direction;

a positioning column is provided at a bottom face of the positioning slot of the moving member corresponding to the elastic member one by one, the elastic member is mounted around the positioning column, the connecting portion defines a guiding groove corresponding to the positioning column, the positioning column is capable of sliding in the guiding groove, and the elastic member is compressed when the operating member is pressed to move towards the moving member.

* * * * *